United States Patent
Kilgore et al.

(10) Patent No.: US 10,807,921 B2
(45) Date of Patent: Oct. 20, 2020

(54) CATALYST SYSTEMS AND ETHYLENE OLIGOMERIZATION METHOD

(71) Applicant: Chevron Phillips Chemical Company LP, The Woodlands, TX (US)

(72) Inventors: Uriah J. Kilgore, Kingwood, TX (US); Steven M. Bischof, Humble, TX (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 163 days.

(21) Appl. No.: 15/828,921

(22) Filed: Dec. 1, 2017

(65) Prior Publication Data
US 2019/0169086 A1 Jun. 6, 2019

(51) Int. Cl.
| | |
|---|---|
| C07C 2/36 | (2006.01) |
| B01J 31/18 | (2006.01) |
| B01J 31/24 | (2006.01) |
| C07F 11/00 | (2006.01) |
| C08F 4/78 | (2006.01) |
| C07C 11/02 | (2006.01) |
| C08F 10/02 | (2006.01) |

(52) U.S. Cl.
CPC ............ *C07C 2/36* (2013.01); *B01J 31/189* (2013.01); *B01J 31/2461* (2013.01); *C07F 11/00* (2013.01); *C08F 4/78* (2013.01); *B01J 2231/20* (2013.01); *B01J 2531/62* (2013.01); *B01J 2540/10* (2013.01); *B01J 2540/30* (2013.01); *B01J 2540/40* (2013.01); *C07C 11/02* (2013.01); *C07C 2523/26* (2013.01); *C07C 2531/14* (2013.01); *C07C 2531/24* (2013.01); *C08F 10/02* (2013.01); *C08F 2500/02* (2013.01)

(58) Field of Classification Search
None
See application file for complete search history.

(56) References Cited

U.S. PATENT DOCUMENTS

| | | | |
|---|---|---|---|
| 6,046,211 A | 4/2000 | Hansen, Jr. et al. | |
| 8,680,003 B2 | 3/2014 | Sydora et al. | |
| 8,865,610 B2 | 10/2014 | Sydora et al. | |
| 9,283,555 B2 | 3/2016 | Sydora et al. | |
| 9,732,106 B2 | 8/2017 | Sydora et al. | |
| 2007/0149582 A1 | 6/2007 | Kordes et al. | |
| 2012/0309965 A1* | 12/2012 | Sydora | C07F 9/46 544/64 |
| 2013/0331629 A1 | 12/2013 | Sydora et al. | |
| 2016/0375431 A1 | 12/2016 | Carney et al. | |
| 2017/0349505 A1 | 12/2017 | Kilgore et al. | |

FOREIGN PATENT DOCUMENTS

| | | |
|---|---|---|
| WO | 2011082192 A1 | 7/2011 |
| WO | 2013184579 A1 | 12/2013 |
| WO | 2017209959 A1 | 12/2017 |

OTHER PUBLICATIONS

Milton et al. Inorgnica Chimica Acta, 358, 1393-1400). (Year: 2005).*
Zhang et al. Organometallics, 2010, 29, 6660-6667 (Year: 2010).*
Braunstein, Pierre, et. al. "Synthesis of Nickel Phenyl Complexes with New Chelating κ2-P,N Ligands Derived from α-Iminoazatriphenylphosphoranes. [Erratum to document cited in CA127:17791]," Journal of Organometallic Chemistry, 1999, vol. 582, p. 370, Elsevier Science S.A.
Braunstein, Pierre, et. al. "Synthesis of Nickel Phenyl Complexes with New Chelating κ2-P,N Ligands Derived from α-Iminoazatriphenylphosphoranes," Journal of Organometallic Chemistry, 1999, vol. 582, pp. 371-377, Elsevier Science S.A.
Braunstein, Pierre, et. al., "Synthesis of Nickel Phenyl Complexes with New Chelating κ2-P,N Ligands Derived from α-Iminoazatriphenylphosphoranes," Journal of Organometallic Chemistry, 1997, vol. 529, pp. 387-393, Elsevier Science S.A.
Buckley, G. D., et al., "Aliphatic Nitro-compounds. Part XV. Preparation of Heterocyclic Bases by Reduction of Nitroalkyl Cyanides," 1947, pp. 1508-1511, Imperial Chemical Industries Limited, Research Laboratories, United Kingdom.
Dyer, Philip W., et al.,"Rigid N-Phosphino Guanidine P,N Ligands and Their Use in Nickel-Catalyzed Ethylene Oligomerization," Organometallics, 2008, vol. 27, pp. 5082-5087, American Chemical Society.

(Continued)

*Primary Examiner* — Yun Qian
(74) *Attorney, Agent, or Firm* — Conley Rose, P.C.

(57) ABSTRACT

Disclosed herein is a catalyst system comprising (i) a heterocyclic 2-[(phosphinyl)aminyl]imine transition metal compound complex having Structure I wherein T is oxygen or sulfur, $R^1$ and $R^2$ are each independently a $C_1$ to $C_{20}$ organyl group consisting essentially of inert functional groups, $R^3$ is hydrogen or a $C_1$ to $C_{20}$ organyl group, L is a $C_1$ to $C_{20}$ organylene group consisting essentially of inert functional groups, $MX_p$ represents a transition metal compound where M is a transition metal, X is a monoanion, and p is an integer from 1 to 6, Q is a neutral ligand, and q ranges from 0 to 6, and (ii) an organoaluminum compound. Also disclosed herein is a process comprising contacting (i) ethylene, (ii) a catalyst system comprising (a) a heterocyclic transition metal compound complex having Structure I as described herein and (b) an organoaluminum compound, and (iii) optionally hydrogen to form an oligomer product.

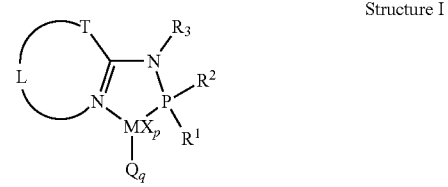

Structure I

23 Claims, No Drawings

(56) References Cited

OTHER PUBLICATIONS

Foreign communication from a related counterpart application—International Search Report and Written Opinion, PCT/US2017/033162, dated Jun. 30, 2017, 10 pages.

Gong, D., et al., "Ethylene polymerization by PN3-type pincer chromium(III) complexes," Journal of Molecular Catalysis A: Chemical, 2014, pp. 100-107, vol. 395, Elsevier B. V.

"Group notation revised in periodic table," Feb. 4, 1985, C&EN, pp. 26-27.

McGuinness, D. S., et al., "Novel CR-PNP complexes as catalysts for the trimerisation of ethylene," Chemical Communications—CHEMCOM, Jan. 1, 2003, pp. 334-335, The Royal Society of Chemistry.

McNaught, Alan D., et al., "Compendium of Chemical Terminology," IUPAC Recommendations, Second edition, 1997, 5 pages, Wiley-Blackwell.

Shankaran, K, et al., "Evaluation of pyrrolidin-2-imines and 1,3-thiazolidin-2-imines as inhibitors of nitric oxide synthase," Bioorganic & Medicinal Chemistry Letters, 2004, pp. 4539-4544, vol. 14, Elsevier Ltd.

Voß, Corinna, et al., Intramolecular d10-d10 interactions in neutral, dinuclear Au(I) complexes supported by amino-thiazoline- and -thiazole-based P,N-phosphine ligands, C.R. Chimie, vol. 15, 2012, pp. 229-236, Elsevier Masson SAS.

Zhang, Shuanming, et al., "Reactions of a Phosphinoimino-thiazoline-Based Metalloligand with Organic and Inorganic Electrophiles and Metal-Induced Ligand Rearrangements," Organometallics, 2010, vol. 29, pp. 6660-6667, American Chemical Society.

Office Action dated May 15, 2018 (39 pages), U.S. Appl. No. 15/171,170, filed Jun. 2, 2016.

\* cited by examiner

CATALYST SYSTEMS AND ETHYLENE OLIGOMERIZATION METHOD

CROSS-REFERENCE TO RELATED APPLICATIONS

Not applicable.

TECHNICAL FIELD

The present disclosure relates to processes for producing ethylene oligomers. More particularly, the present disclosure relates to improved ethylene oligomerization catalyst systems comprising heterocyclic 2-[(phosphinyl)aminyl]imines and heterocyclic 2-[(phosphinyl)aminyl]imine transition metal compound complexes and their use in processes for oligomerizing ethylene.

BACKGROUND

Olefins, also commonly known as alkenes, are important items of commerce. Their many applications include employment as intermediates in the manufacture of detergents, as precursors to more environmentally-friendly refined oils, as monomers, and as precursors for many other types of products. An important subset of olefins are alpha olefins, and one process of making alpha olefins is via oligomerization of ethylene, which is a catalytic reaction involving various types of catalysts and/or catalyst systems. Examples of catalysts and catalyst systems used commercially to produce alpha olefins include alkylaluminum compounds, certain nickel-phosphine complexes, titanium halides with a Lewis acid (e.g., diethyl aluminum chloride), zirconium halides and/or zirconium alkoxides with alkylaluminum compounds. Additionally, there is a selective ethylene trimerization and/or tetramerization catalyst system for producing 1-hexene that uses a chromium containing compound (e.g., a chromium carboxylate), a nitrogen-containing ligand (e.g., a pyrrole), and a metal alkyl (e.g., an alkyl aluminum compound), and a selective trimerization and/or tetramerization catalyst system using a metal complex of a compound having a diphosphinylaminyl group.

Several other ethylene oligomerization catalyst systems which can be utilized to produce alpha olefins are based upon metal complexes of pyridine bis-imines, metal complexes of α-diimine compounds having a metal complexing group, and selective trimerization and/or tetramerization catalyst systems using a metal compound (e.g., a chromium compound) complex of a diphosphinylamine, phosphinyl formamidine, phosphinyl amidine, or phosphinyl guanidine. These catalyst systems typically use an organoaluminum compound (e.g., an aluminoxane) as a component of the catalyst systems for olefin oligomerization.

Applications and demand for olefins (e.g., alpha olefins) continue to multiply, and competition to supply them correspondingly intensifies. Thus, additional novel catalyst systems and processes for olefin oligomerization are desirable.

SUMMARY

Disclosed herein is a catalyst system comprising (i) a heterocyclic 2-[(phosphinyl)aminyl]imine transition metal compound complex having Structure HCPAITMC 1 wherein T is oxygen or sulfur, $R^1$ and $R^2$ are each independently a $C_1$ to $C_{20}$ organyl group consisting essentially of inert functional groups, $R^3$ is hydrogen or a $C_1$ to $C_{20}$ organyl group, L is a $C_1$ to $C_{20}$ organylene group consisting essentially of inert functional groups, $MX_p$ represents a transition metal compound where M is a transition metal, X is a monoanion, and p is an integer from 1 to 6, Q is a neutral ligand, and q ranges from 0 to 6, and (ii) an organoaluminum compound.

Also disclosed herein is a process comprising contacting (i) ethylene, (ii) a catalyst system comprising (a) a heterocyclic 2-[(phosphinyl)aminyl]imine transition metal compound complex having Structure HCPAITMC 1 wherein T is oxygen or sulfur, $R^1$ and $R^2$ are each independently a $C_1$ to $C_{20}$ organyl group consisting essentially of inert functional groups, $R^3$ is hydrogen or a $C_1$ to $C_{20}$ organyl group, L is a $C_1$ to $C_{20}$ organylene group consisting essentially of inert functional groups, $MX_p$ represents a transition metal compound where M is a transition metal, X is a monoanion, and p is an integer from 2 to 6, Q is a neutral ligand, q ranges from 0 to 6, and (b) an organoaluminum compound, and (iii) optionally hydrogen to form an oligomer product.

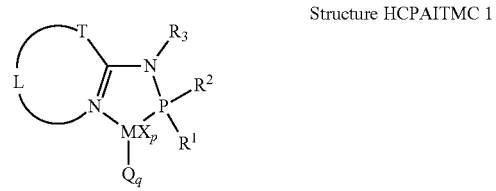

Structure HCPAITMC 1

DETAILED DESCRIPTION

In the description herein, various ranges and/or numerical limitations can be expressly stated. It should be recognized that unless stated otherwise, it is intended that endpoints are to be interchangeable. Further, any ranges include iterative ranges of like magnitude falling within the expressly stated ranges or limitations.

Furthermore, various modifications can be made within the scope of the presently described subject matter as herein intended, and embodiments of the present disclosure can include combinations of features other than those expressly claimed. In particular, flow arrangements other than those expressly described herein are within the scope of the present disclosure.

Regarding claim transitional terms or phrases, the transitional term "comprising", which is synonymous with "including," "containing," "having" or "characterized by," is inclusive or open-ended and does not exclude additional, unrecited elements or process steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the present disclosure. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter compositions or processes to which the term is applied. For example, a feedstock consisting essentially of a material A can include impurities typically present in a commercially produced or commercially available sample of the material A. When a claim includes different features and/or feature classes (for example, a process step, feedstock features, and/or product features, among other possibilities), the transitional terms "comprising," "consisting essentially of," and "consisting of" apply only to the feature class that is utilized and it is possible to have different transitional terms or phrases utilized with different feature classes within a claim. For example, a process can comprise several recited steps (and other non-recited steps), but can utilize a catalyst system preparation consisting of specific steps and/or can utilize a catalyst system comprising recited components and other non-recited components.

Within this specification, use of "comprising" or an equivalent expression contemplates the use of the phrase "consisting essentially of," "consists essentially of," or equivalent expressions as alternative embodiments to the open-ended expression. Additionally, use of "comprising" or an equivalent expression or use of "consisting essentially of" in the specification contemplates the use of the phrase "consisting of," "consists of," or equivalent expressions as an alternative to the open-ended expression or middle ground expression, respectively. For example, "comprising" should be understood to include "consisting essentially of," and "consisting of" as alternative embodiments for the aspect, features, and/or elements presented in the specification unless specifically indicated otherwise.

While compositions and processes are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound unless otherwise specified.

Unless otherwise indicated, the definitions set forth herein are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition can be applied. To the extent that any definition or usage provided by any document incorporated herein by reference conflicts with the definition or usage provided herein, the definition or usage provided herein controls.

Groups of elements of the Periodic Table are indicated using the numbering scheme indicated in the version of the Periodic Table of elements published in *Chemical and Engineering News*, 63(5), 27, 1985. In some instances, a group of elements can be indicated using a common name assigned to the group; for example, alkali metals for Group 1 elements, alkaline earth metals (or alkaline metals) for Group 2 elements, transition metals for Groups 3-12 elements, and halogens for Group 17 elements.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to hexene includes 1-hexene, 2-hexene, 3-hexene, and any other hydrocarbon having 6 carbon atoms (linear, branched or cyclic) and only one carbon-carbon double bond. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") of hydrogen atoms from a parent compound, which in this example can be described as an "alkane group," and which encompasses an "alkyl group," an "alkylene group," and materials having three or more hydrogens atoms, as necessary for the situation, removed from the alkane. Throughout, the disclosure of a substituent, ligand, or other chemical moiety that can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "substituted" when used to describe a compound or group, for example, when referring to a substituted analog of a particular compound or group, is intended to describe any non-hydrogen moiety that formally replaces a hydrogen atom in that group, and is intended to be non-limiting. A group or groups can also be referred to herein as "unsubstituted" or by equivalent terms such as "non-substituted," which refers to the original group in which a non-hydrogen moiety does not replace a hydrogen atom within that group. "Substituted" is intended to be non-limiting and can include inorganic substituents or organic substituents.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which participates in the processes described herein and does not substantially interfere with the processes described herein and/or does not complex with a metal compound of a metal complex. The term "does not complex with a metal compound" can apply to groups that could complex with the metal compound but (in particular molecules described herein), may not complex with the metal compound due to its location within a ligand. For example, while an ether group can complex with the metal compound, an ether group located at a para position of a substituted phenyl phosphinyl group in a 2-((phosphinyl)aminyl)-oxazole can be an inert functional group because the single metal compound cannot complex with both the para ether group and both nitrogen atoms of the 2-((phosphinyl)aminyl)-oxazole in a single metal compound complex molecule. Thus, the inertness of a particular functional group is related not only to the functional group's inherent inability to complex the metal compound but can be related also to the functional group's position within the metal compound complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), sulfidyl groups, and/or hydrocarbyl groups, among others.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g., halogenated alkane indicates the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

A "cycloalkane" is a saturated cyclic hydrocarbon, with or without side chains, for example, cyclobutane. Unsaturated cyclic hydrocarbons having one or more endocyclic double or one triple bond are called cycloalkenes and cycloalkynes, respectively. Cycloalkenes and cycloalkynes having only one, only two, only three, etc . . . endocyclic double or triple bonds, respectively, can be identified by use of the term "mono," "di," "tri," etc. within the name of the cycloalkene or cycloalkyne. Cycloalkenes and cycloalkynes can further identify the position of the endocyclic double or triple bonds.

A "cycloalkyl group" is a univalent group derived by removing a hydrogen atom from a ring carbon atom of a cycloalkane. For example, a 1-methylcyclopropyl group and a 2-methylcyclopropyl group are illustrated as follows.

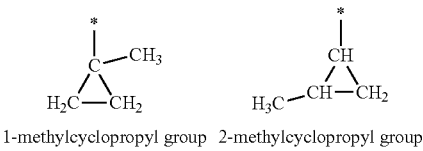

1-methylcyclopropyl group  2-methylcyclopropyl group

Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane. It should be noted that according to the definitions provided herein, general cycloalkane groups (including cycloalkyl groups and cycloalkylene groups), include those having zero, one, or more than one hydrocarbyl substituent groups attached to a cycloalkane ring carbon atom (e.g., a methylcyclopropyl group), and are members of the group of hydrocarbon groups. However, when referring to a cycloalkane group having a specified number of cycloalkane ring carbon atoms (e.g., cyclopentane group or cyclohexane group, among others), the base name of the cycloalkane group having a defined number of cycloalkane ring carbon atoms refers to the unsubstituted cycloalkane group (including having no hydrocarbyl groups located on cycloalkane group ring carbon atom). Consequently, a substituted cycloalkane group having a specified number of ring carbon atoms (e.g., substituted cyclopentane or substituted cyclohexane, among others) refers to the respective group having one or more substituent groups (including halogens, hydrocarbyl groups, or hydrocarboxy groups, among other substituent groups) attached to a cycloalkane group ring carbon atom. When the substituted cycloalkane group having a defined number of cycloalkane ring carbon atoms is a member of the group of hydrocarbon groups (or a member of the general group of cycloalkane groups), each substituent of the substituted cycloalkane group having a defined number of cycloalkane ring carbon atoms is limited to a hydrocarbyl substituent group. One can readily discern and select general groups, specific groups, and/or individual substituted cycloalkane group(s) having a specific number of ring carbons atoms which can be utilized as member of the hydrocarbon group (or a member of the general group of cycloalkane groups).

An aliphatic compound is an acyclic or cyclic, saturated or unsaturated carbon compound, excluding aromatic compounds. An "aliphatic group" is a generalized group formed by removing one or more hydrogen atoms (as necessary for the particular group) from the carbon atom of an aliphatic compound. Aliphatic compounds and therefore aliphatic groups can contain organic functional group(s) and/or atom(s) other than carbon and hydrogen.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "alkene" whenever used in this specification and claims refers to a cyclic and acyclic, and/or linear or branched aliphatic hydrocarbon olefin that has one or more carbon-carbon double bonds. Alkenes having only one, only two, only three, etc., such multiple bonds can be identified by use of the term "mono," "di," "tri," etc., within the name. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2 position (a vinylidene) and/or the 3-position or higher with respect to the olefin double bond. The term "vinylidene" whenever used in this specification and claims refers to an alpha olefin having a branch at the 2 position with respect to the olefin double bond. By itself, the term "alpha olefin" does not indicate the presence or absence of other carbon-carbon double bonds unless explicitly indicated.

The term "normal alpha olefin" whenever used in this specification and claims refers to a linear aliphatic monoolefin having a carbon-carbon double bond between the first and second carbon atoms. It is noted that "normal alpha olefin" is not synonymous with "linear alpha olefin" as the term "linear alpha olefin" can include linear olefinic compounds having a double bond between the first and second carbon atoms and additional double bonds.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" (heteroaromatic compounds formally derived from arenes by replacement of one or more methine (—C═) carbon atoms of the cyclically conjugated double bond system with a trivalent or divalent heteroatom, in such a way as to maintain the continuous pi-electron system characteristic of an aromatic system and a number of out-of-plane pi-electrons corresponding to the Hückel rule (4n+2). While arene compounds and heteroarene compounds are mutually exclusive members of the group of aromatic compounds, a compound that has both an arene group and a heteroarene group is generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon—the methylene group in diphenylmethane; oxygen—diphenyl ether; nitrogen—triphenyl amine; among other linking groups). As disclosed herein, the term "substituted" can be used to describe an aromatic group, arene, or heteroarene wherein a non-hydrogen moiety formally replaces a hydrogen in the compound, and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" can have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

An "aralkyl group" is an aryl-substituted alkyl group having a free valance at a non-aromatic carbon atom (e.g. a benzyl group, or a 2-phenyleth-1yl group, among others). Similarly, an "aralkylene group" is an aryl-substituted alkylene group having two free valencies at a single non-aromatic carbon atom or a free valence at two non-aromatic carbon atoms while an "aralkane group" is an aryl-substituted alkane group having one or more free valencies at a non-aromatic carbon atom(s). It should be noted that according the definitions provided herein, general aralkane groups include those having zero, one, or more than one hydrocarbyl substituent groups located on an aralkane aromatic hydrocarbon ring or ring system carbon atom and are members of the group of hydrocarbon groups. However, specific aralkane groups specifying a particular aryl group (e.g. the phenyl group in a benzyl group or a 2-phenylethyl group, among others) refer to the specific unsubstituted aralkane groups (including no hydrocarbyl group located on the aralkane aromatic hydrocarbon ring or ring system carbon atom). Consequently, a substituted aralkane group specifying a particular aryl group refers to a respective aralkane group having one or more substituent groups (including halogens, hydrocarbyl groups, or hydrocarboxy groups, among others). When the substituted aralkane group specifying a particular aryl group is a member of the group of hydrocarbon groups (or a member of the general group of aralkane groups), each substituent is limited to a hydrocarbyl substituent group. One can readily discern and select substituted aralkane groups specifying a particular aryl group which can be utilized as a member of the group of hydrocarbon groups (or a member of the general group of aralkane groups).

A "halide" has its usual meaning; therefore, examples of halides include fluoride, chloride, bromide, and iodide.

As used herein, a heterocyclic 2-[(phosphinyl)aminyl] imine is an imine compound (i.e., a compound having a carbon-nitrogen double bond) where the carbon atom and the nitrogen atom of the imine group and one other heteroatom attached to the carbon atom of the imine group are contained within a single ring or a single ring of a ring system. Additionally, as described herein the heterocyclic 2-[(phosphinyl)aminyl]imine has a phosphinylaminyl group located on the carbon atom of the imine carbon-nitrogen double bond. As such, a "heterocyclic 2-[(phosphinyl)aminyl]imine transition metal compound complex" and its derivations is a complex between a transition metal compound and a heterocyclic 2-[(phosphinyl)aminyl]imine. For the purpose of this application, the ring containing the carbon atom and the nitrogen atom of the imine group and one other heteroatom attached to the carbon atom of the imine group does not include a metal atom (e.g., a ring formed by transition metal compound and a amidine compound or a $N^2$-phosphinyl amidine compound, among others).

Within this disclosure the normal rules of organic chemistry nomenclature prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. References to compounds or groups having substitution at positions in addition to the indicated position can be referenced using "comprising" or some other alternative language. For example, a reference to a phenyl group "comprising a substituent at the 4 position" refers to a phenyl group having a non-hydrogen substituent group at the 4 position and hydrogen or any non-hydrogen group at the 2, 3, 5, and 6 positions.

The term "reaction zone effluent," and its derivatives generally refers to all materials which exit the reaction and can include reaction system feed(s) (e.g., ethylene, catalyst system or catalyst system components, and/or organic reaction medium), and/or reaction product(s) (e.g., oligomer product including oligomers and non-oligomers). The term "reaction zone effluent" and its derivatives can be qualified to refer to certain portions by use of additional qualifying terms. For example, while "reaction zone effluent" refers to all material which exits the reaction system through the reaction zone outlet/discharge, a "reaction zone oligomer product effluent" refers to only the oligomer product within the reaction zone effluent.

The terms "room temperature" or "ambient temperature" are used herein to describe any temperature from about 15° C. to about 35° C. wherein no external heat or cooling source is directly applied. Accordingly, the terms "room temperature" and "ambient temperature" encompass the individual temperatures and any and all ranges, subranges, and combinations of subranges of temperatures from about 15° C. to about 35° C. wherein no external heating or cooling source is directly applied. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

Processes and/or methods described herein can utilize steps, features, and compounds which are independently described herein. The process and/or methods described herein may or may not utilize step identifiers (e.g., 1), 2), etc., a), b), etc., i), ii), etc., or first, second, etc., among others), feature identifiers (e.g., 1), 2), etc., a), b), etc., i), ii), etc., or first, second, etc., among others), and/or compound and/or composition identifiers (e.g., 1), 2), etc., a), b), etc., i), ii), etc., or first, second, etc., among others). However, it should be noted that processes and/or methods described herein can have multiple steps, features (e.g., reagent ratios, formation conditions, among other considerations), and/or multiple compounds and/or compositions using no descriptor or sometimes having the same general identifier. Consequently, it should be noted that the processes and/or methods described herein can be modified to use an appropriate step or feature identifier (e.g., 1), 2), etc., a), b), etc., i), ii), etc., or first, second, etc., among others), feature identifier (e.g., 1), 2), etc., a), b), etc., i), ii), etc., or first, second, etc., among others), and/or compound identifier (e.g., first, second, etc.) regardless of step, feature, and/or compound identifier utilized in a particular aspect and/or embodiment described herein and that step or feature identifiers can be added and/or modified to indicate individual different steps/features/compounds utilized within the process and/or methods without detracting from the general disclosure.

Processes of forming oligomer products are described herein. Such processes generally comprise contacting ethylene and a catalyst system (or catalyst system components) to form an oligomer product under oligomerization conditions. As used herein, the term "oligomerization" and its derivatives, refers to processes which produce a mixture of products containing at least 70 weight percent products containing from 2 to 30 ethylene units. Similarly, as used herein, an "oligomer" is a product that contains from 2 to 30 ethylene units while an "oligomer product" includes all products made by the process including the "oligomers" and products which are not "oligomers" (e.g., products which contain more than 30 monomer units). Further the terms "oligomer product" and "oligomerization product" can be used interchangeably.

As used herein, the term "trimerization," and its derivatives, refers to a process which produces a mixture of products containing at least 70 weight percent products containing three and only three ethylene units. As used herein, a "trimer" is a product which contains three and only three ethylene units while a "trimerization product" includes all products made by the trimerization process including the trimer and products which are not trimers (e.g., dimers or tetramers). Generally, a "trimerization" process using ethylene produces an oligomer product containing at least 70 weight percent hexene(s).

As used herein, the term "tetramerization," and its derivatives, refers to a process which produces a mixture of products containing at least 70 weight percent products containing four and only four ethylene units. As used herein, a "tetramer" is a product which contains four and only four ethylene units while a "tetramerization product" includes all products made by the tetramerization process including the tetramer and products which are not tetramers (e.g., dimers or trimers). Generally, a "tetramerization" process using ethylene produces an oligomer product containing at least 70 weight percent octene(s).

As used herein, the term "trimerization and tetramerization," and its derivatives, refers to a process which produces an oligomer product containing at least 70 weight percent products containing three and/or four and only three and/or four ethylene units. As used herein, a "trimerization and tetramerization product" includes all products made by the "trimerization and tetramerization" process including trimer, tetramer, and products which are not trimers or tetramers (e.g., dimers). Generally, a "trimerization and tetramerization" process using ethylene produces an oligomer product containing at least 70 weight percent hexene(s) and/or octene(s).

Unless otherwise specified, the terms "contacted," "combined," and "in the presence of" refer to any addition sequence, order, or concentration for contacting or combining two or more components of the oligomerization process. Combining or contacting of oligomerization components, according to the various methods described herein, can occur in one or more contact zones under suitable contact conditions such as temperature, pressure, contact time, flow rates, etc. The contact zone can be disposed in a vessel (e.g., a storage tank, tote, container, mixing vessel, reactor, etc.), a length of pipe (e.g., a tee, inlet, injection port, or header for combining component feed lines into a common line), or any other suitable apparatus for bringing the components into contact. The processes can be carried out in a batch or continuous process as can be suitable for a given embodiment.

Embodiments disclosed herein can provide the materials listed as suitable for satisfying a particular feature of the embodiment delimited by the term "or." For example, a particular feature of the disclosed subject matter can be disclosed as follows: Feature X can be A, B, or C. It is also contemplated that for each feature the statement can also be phrased as a listing of alternatives such that the statement "Feature X is A, alternatively B, or alternatively C" is also an embodiment of the present disclosure whether or not the statement is explicitly recited.

Features within this disclosure that are provided as minimum values can be alternatively stated as "at least" or "greater than or equal to" any recited minimum value for the features disclosed herein. Features within this disclosure that are provided as maximum values can be alternatively stated as "less than or equal to" any recited maximum value for the feature disclosed herein.

Use of the term "optionally" with respect to any element of a claim is intended to mean that the subject element can be required, or alternatively, may not be required. Both alternatives are intended to be within the scope of the claim.

Aspects of this disclosure are directed to catalyst systems comprising i) a heterocyclic 2-[(phosphinyl)aminyl]imine transition metal compound complex, and ii) an organoaluminum compound. In additional aspects, this disclosure is directed to processes comprising contacting i) ethylene, ii) a catalyst system comprising a heterocyclic 2-[(phosphinyl)aminyl]imine transition metal compound complex and an organoaluminum compound, and iii) optionally hydrogen to form an oligomer product. Generally, the heterocyclic 2-[(phosphinyl)aminyl]imine transition metal compound complex, the organoaluminum compound, any other catalyst system component(s) described herein, and any catalyst system component ratio(s) described herein are independent elements of the catalyst systems. These catalyst system elements are independently described herein and can be utilized without limitation, and in any combination, to further describe the catalyst systems utilized in aspects and/or embodiments described herein.

The heterocyclic 2-[(phosphinyl)aminyl]imine transition metal compound complexes utilized in the catalyst systems and/or the processes described herein can have general Structure HCPAITMC 1. In an embodiment, the heterocyclic 2-[(phosphinyl)aminyl]imine transition metal compound complexes utilized in the catalyst systems and/or the processes described herein can have Structure HCPAITMC 2, Structure HCPAITMC 3, Structure HCPAITMC 4, Structure HCPAITMC 5, or Structure HCPAITMC 6; alternatively, Structure HCPAITMC 2, Structure HCPAITMC 3, or Structure HCPAITMC 5; alternatively, Structure HCPAITMC 4 or Structure HCPAITMC 6; alternatively, Structure HCPAITMC 2 or Structure HCPAITMC 3; alternatively, Structure HCPAITMC 2; alternatively, Structure HCPAITMC 3; alternatively, Structure HCPAITMC 4; alternatively, Structure HCPAITMC 5; or alternatively, Structure HCPAITMC 6. In other embodiments, the heterocyclic 2-[(phosphinyl)aminyl]imine transition metal compound complexes utilized in the catalyst systems and/or the processes described herein can have Structure HCPAITMC 7, Structure HCPAITMC 8, Structure HCPAITMC 9, Structure HCPAITMC 10, or Structure HCPAITMC 11; alternatively, Structure HCPAITMC 7, Structure HCPAITMC 8, or Structure HCPAITMC 10; alternatively, Structure HCPAITMC 9, or Structure HCPAITMC 11; alternatively, Structure HCPAITMC 7; alternatively, Structure HCPAITMC 8; alternatively, Structure HCPAITMC 9; alternatively, Structure HCPAITMC 10; or alternatively, Structure HCPAITMC 11.

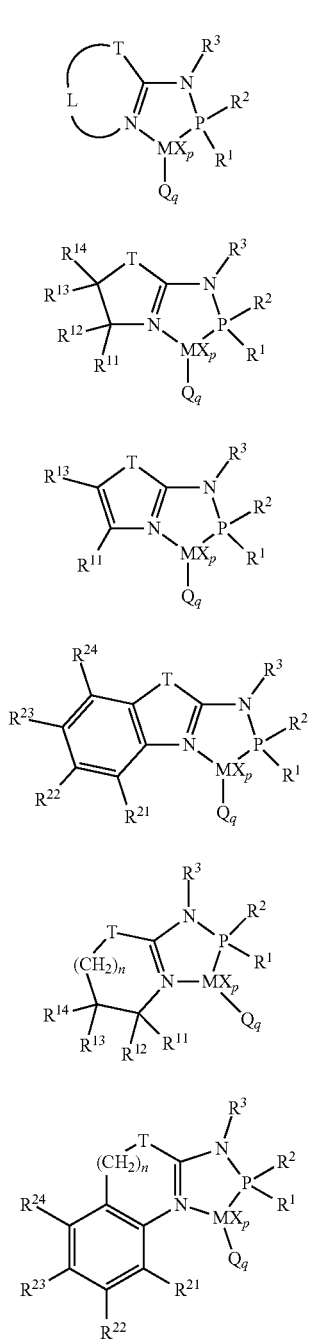

Structure HCPAITMC 1

Structure HCPAITMC 2

Structure HCPAITMC 3

Structure HCPAITMC 4

Structure HCPAITMC 5

Structure HCPAITMC 6

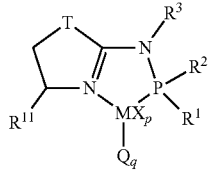

Structure HCPAITMC 7

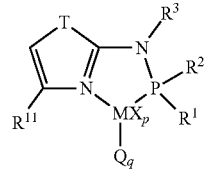

Structure HCPAITMC 8

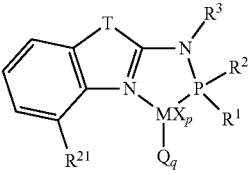

Structure HCPAITMC 9

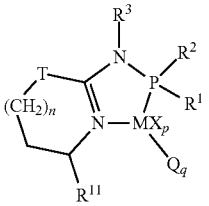

Structure HCPAITMC 10

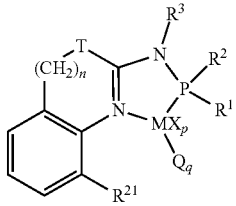

Structure HCPAITMC 11

$R^1$, $R^2$, $R^3$, $R^{11}$, $R^{12}$, $R^{13}$, $R^{14}$, $R^{21}$, $R^{22}$, $R^{23}$, $R^{24}$, T, L, Q, q, and the transition metal compound $MX_p$ within the heterocyclic 2-[(phosphinyl)aminyl]imine transition metal compound complexes described herein are independent elements of the heterocyclic 2-[(phosphinyl)aminyl]imine transition metal compound complex structure in which they are present and are independently described herein. The independent descriptions of $R^1$, $R^2$, $R^3$, $R^{11}$, $R^{12}$, $R^{13}$, $R^{14}$, $R^{21}$, $R^{22}$, $R^{23}$, $R^{24}$, T, L, Q, q, and/or the transition metal compound $MX_p$ provided herein can be utilized without limitation, and in any combination, to further describe any heterocyclic 2-[(phosphinyl)aminyl]imine transition metal compound complex structures which comprise an $R^1$, $R^2$, $R^3$, $R^{11}$, $R^{12}$, $R^{13}$, $R^{14}$, $R^{21}$, $R^{22}$, $R^{23}$, $R^{24}$, L, Q, and/or q, and the transition metal compound $MX_p$.

Generally, T of the heterocyclic 2-[(phosphinyl) aminyl]imine transition metal compound complexes can be oxygen or sulfur. In some embodiments, T of the heterocyclic 2-[(phosphinyl)aminyl]imine transition metal compound complexes can be oxygen; or alternatively, sulfur.

Generally, $R^1$ and/or $R^2$ of the heterocyclic 2-[(phosphinyl)aminyl]imine transition metal compound complexes independently can be an organyl group; alternatively, an organyl group consisting essentially of inert functional groups; or alternatively, a hydrocarbyl group. In an embodiment, the $R^1$ and/or $R^2$ organyl groups of the heterocyclic 2-[(phosphinyl)aminyl]imine transition metal compound complexes can be a $C_1$ to $C_{20}$, a $C_1$ to $C_{10}$, or a $C_1$ to $C_5$ organyl group. In an embodiment, the $R^1$ and/or $R^2$ organyl groups consisting essentially of inert functional groups of the heterocyclic 2-[(phosphinyl)aminyl]imine transition metal compound complexes independently can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, the $R^1$ and/or $R^2$ hydrocarbyl groups of the heterocyclic 2-[(phosphinyl)aminyl]imine transition metal compound complexes independently can be a $C_1$ to $C_{20}$, a $C_1$ to $C_{15}$, a $C_1$ to $C_{10}$, or a $C_1$ to $C_5$ hydrocarbyl group. In further embodiments, the $R^1$ and $R^2$ groups of the heterocyclic 2-[(phosphinyl)aminyl]imine transition metal compound complexes can be joined to form a ring or a ring system (regardless of particular type of group—organyl, organyl consisting of inert functional groups, or hydrocarbyl group, including any species, sub-species, or individuals contained therein and/or described herein) containing the phosphorus atom of the heterocyclic 2-[(phosphinyl)aminyl] imine.

In an embodiment, $R^1$ and/or $R^2$ of any heterocyclic 2-[(phosphinyl)aminyl]imine transition metal compound complex can be an alkyl group, a substituted alkyl group, a cycloalkyl group, a substituted cycloalkyl group, an aryl group, a substituted aryl group, an aralkyl group, or a substituted aralkyl group. In some embodiments, $R^1$ and/or $R^2$ of any heterocyclic 2-[(phosphinyl)aminyl]imine transition metal compound complex can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^1$ and/or $R^2$ of any heterocyclic 2-[(phosphinyl)aminyl]imine transition metal compound complex independently can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect or embodiment disclosed herein, each alkyl group which can be utilized as $R^1$ and/or $R^2$ independently can be a $C_1$ to $C_{20}$, a $C_1$ to $C_{10}$, or a $C_1$ to $C_5$ alkyl group. In any aspect or embodiment disclosed herein, each substituted alkyl group which can be utilized as $R^1$ and/or $R^2$ independently can be a $C_1$ to $C_{20}$, a $C_1$ to $C_{10}$, or a $C_1$ to $C_5$ substituted alkyl group. In any aspect or embodiment disclosed herein, each cycloalkyl group which can be utilized as $R^1$ and/or $R^2$ independently can be a $C_4$ to $C_{20}$, a $C_4$ to $C_{15}$, or a $C_4$ to $C_{10}$ cycloalkyl group. In any aspect or embodiment disclosed herein, each substituted cycloalkyl group which can be utilized as $R^1$ and/or $R^2$ independently can be a $C_4$ to $C_{20}$, a $C_4$ to $C_{15}$, or a $C_4$ to $C_{10}$ substituted cycloalkyl group. In any aspect or embodiment disclosed herein, each aryl group which can be utilized as $R^1$ and/or $R^2$ independently can be a $C_6$ to $C_{20}$, a $C_6$ to $C_{15}$, or a $C_6$ to $C_{10}$ aryl group. In any aspect or embodiment disclosed herein, each substituted aryl group which can be utilized as $R^1$ and/or $R^2$ independently can be a $C_6$ to $C_{20}$, a $C_6$ to $C_{15}$, or a $C_6$ to $C_{10}$ substituted aryl group. In any aspect or embodiment disclosed herein, each aralkyl group which can be utilized $R^1$ and/or $R^2$ independently can be a $C_7$ to $C_{20}$, a $C_7$ to $C_{is}$, or a $C_7$ to $C_{10}$ aralkyl group. In any aspect or embodiment disclosed herein, each substituted aralkyl group which can be utilized as $R^1$ and/or $R^2$ independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or a substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^1$ and/or $R^2$.

In an embodiment, $R^1$ and/or $R^2$ independently can be a methyl group, an ethyl group, a propyl group, a butyl group, a pentyl group, a hexyl group, a heptyl group, or an octyl group. In some embodiments, $R^1$ and/or $R^2$ independently can be a methyl group, an ethyl group, an n-propyl (1-propyl) group, an iso-propyl (2-propyl) group, an iso-butyl (2-butyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, an iso-butyl (2-butyl) group; alternatively, a tert-butyl (2-methyl-2-propyl) group; or alternatively, a neopentyl (2,2-dimethyl-1-propyl) group. In some embodiments, the alkyl groups which can be utilized as $R^1$ and/or $R^2$ can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as $R^1$ and/or $R^2$.

In an embodiment, $R^1$ and/or $R^2$ independently can be a cyclopentyl group, a substituted cyclopentyl group, a cyclohexyl group, or a substituted cyclohexyl group; alternatively, a cyclopentyl group or a substituted cyclopentyl group; alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an embodiment, the substituted cycloalkyl group, which can be utilized for $R^1$ and/or $R^2$ can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; alternatively, a 2,6-disubstituted cyclohexyl group or a 2,5-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,5-disubstituted cyclopentyl group. In an embodiment where the substituted cycloalkyl group has more than one substituent, the substituents can be the same or different; alternatively, the same; or alternatively, different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^1$ and/or $R^2$.

In a non-limiting embodiment, $R^1$ and/or $R^2$ independently can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Generally, the alkyl substituents of a disubstituted cyclohexyl group or a disubstituted cyclopentyl group can be the same; or alternatively, the alkyl substituents of a disubstituted cyclohexyl group or disubstituted cyclopentyl group can be different. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^1$ and/or $R^2$. In some non-limiting embodiments, $R^1$ and/or $R^2$ independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting embodiments, $R^1$ and/or $R^2$ independently can be, a 2-methylcyclopentyl group, a 2-ethylcyclopentyl group, a 2-isopropylcyclopentyl group, or a 2-tert-butylcyclopentyl group; or alternatively, a 2,5-dimethylcyclopentyl group, a 2,5-diethylcyclopentyl group, a 2,5-diisopropylcyclopentyl group, or a 2,5-di-tert-butylcyclopentyl group.

In an embodiment, $R^1$ and/or $R^2$ independently can be a phenyl group, or a substituted phenyl group; alternatively, a phenyl group; or alternatively, a substituted phenyl group. In an embodiment, the substituted phenyl group, which can be utilized for $R^1$ and/or $R^2$ can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an embodiment, one or more substituents of a multi-substituted phenyl group utilized as $R^1$ and/or $R^2$ can be the same or different; alternatively, all the substituents of a multi-substituted phenyl group can be the same; or alternatively, all the substituents of a multi-substituted phenyl group can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^1$ and/or $R^2$.

In a non-limiting embodiment, $R^1$ and/or $R^2$ independently can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Generally, the alkyl substituents of a dialkylphenyl group (general or specific) or trialkylphenyl group (general or specific) can be the same; or alternatively, the alkyl substituents of a dialkylphenyl group (general or specific) or trialkylphenyl group (general or specific) can be different. In some non-limiting embodiments, $R^1$ and/or $R^2$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting embodiment, $R^1$ and/or $R^2$ independently can be a phenyl group, a 2-alkoxyphenyl group, or a 4-alkoxyphenyl group. In some non-limiting embodiments, $R^1$ and/or $R^2$ independently can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group.

In a non-limiting embodiment, $R^1$ and/or $R^2$ independently can be a phenyl group, a 2-halophenyl group, a 4-halophenyl group, or a 2,6-dihalophenylgroup. Generally, the halides of a dihalophenyl group can be the same; or alternatively, the halides of a dihalophenyl group can be different. In some embodiments, $R^1$ and/or $R^2$ independently can be a phenyl group, a 2-fluorophenyl group, a 4-fluorophenyl group, or a 2,6-difluorophenyl group.

In an embodiment, $R^1$ and/or $R^2$ independently can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl which can be utilized as $R^1$ and/or $R^2$.

Generally, $R^3$ of any heterocyclic 2-[(phosphinyl)aminyl]imine transition metal compound complex can be hydrogen or an organyl group; alternatively, hydrogen or an organyl group consisting essentially of inert functional groups; alternatively, hydrogen or a hydrocarbyl group; alternatively, hydrogen; alternatively, an organyl group; alternatively, an organyl group consisting essentially of inert functional groups; or alternatively, a hydrocarbyl group. In an embodiment, the organyl group which can be utilized as $R^3$ of the heterocyclic 2-[(phosphinyl)aminyl]imine transition metal compound complexes can be a $C_1$ to $C_{20}$, a $C_1$ to $C_{15}$, a $C_1$ to $C_{10}$, or a $C_1$ to $C_5$ organyl group. In an embodiment, the organyl group consisting essentially of inert functional groups which can utilized as $R^3$ of any heterocyclic 2-[(phosphinyl)aminyl]imine transition metal compound complex can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, the hydrocarbyl group which can be utilized as $R^3$ of any heterocyclic 2-[(phosphinyl)aminyl]imine transition metal compound complex can be a $C_1$ to $C_{20}$, a $C_1$ to $C_{15}$, a $C_1$ to $C_{10}$, or a $C_1$ to $C_5$ hydrocarbyl group. In other embodiments, $R^3$ of any heterocyclic 2-[(phosphinyl)aminyl]imine transition metal compound complex can be a $C_1$ to $C_{20}$, a $C_1$ to $C_{15}$, a $C_1$ to $C_{10}$, or a $C_1$ to $C_5$ alkyl group. In yet another embodiment, $R^3$ of any heterocyclic 2-[(phosphinyl)aminyl]imine transition metal compound complex can be a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. Substituent groups (general and specific) are provided herein and these substituent groups can be utilized to further describe the substituted phenyl groups which can be utilized as $R^3$ of any of the heterocyclic 2-[(phosphinyl) aminyl]imine transition metal compound complexes.

Generally, L of the heterocyclic 2-[(phosphinyl)aminyl]imine transition metal compound complexes having Structure HCPAITMC 1 can be an organylene group; alternatively, an organylene group consisting essentially of inert functional groups; alternatively, a hydrocarbylene group; or alternatively, an alkylene group. In an embodiment, the L organylene group of the heterocyclic 2-[(phosphinyl)aminyl]imine transition metal compound complexes can be a $C_1$ to $C_{20}$, a $C_1$ to $C_{10}$, or a $C_1$ to $C_5$ organylene group. In an embodiment, the L organylene group consisting of inert functional groups of the heterocyclic 2-[(phosphinyl)aminyl]imine transition metal compound complexes independently can be a $C_1$ to $C_{20}$, a $C_1$ to $C_{15}$, a $C_1$ to $C_{10}$, or a $C_1$ to $C_5$ organylene group consisting essentially of inert functional groups. In an embodiment, the L hydrocarbyl group of the heterocyclic 2-[(phosphinyl)aminyl]imine transition metal compound complexes independently can be a $C_1$ to $C_{20}$, a $C_1$ to $C_{15}$, a $C_1$ to $C_{10}$, or a $C_1$ to $C_5$ hydrocarbylene group. In an embodiment, the L alkylene group of the heterocyclic 2-[(phosphinyl)aminyl]imine transition metal compound complexes independently can be a $C_1$ to $C_{20}$, a $C_1$ to $C_{15}$, a $C_1$ to $C_{10}$, or a $C_1$ to $C_5$ alkylene group.

In an embodiment, L of the heterocyclic 2-[(phosphinyl)aminyl]imine transition metal compound complexes having Structure HCPAITMC 1 can have Structure 1L. In some embodiments, L of the heterocyclic 2-[(phosphinyl)aminyl]imine transition metal compound complexes having Structure HCPAITMC 1 can have Structure 2L or Structure 3L; alternatively, Structure 4L, or Structure 6L. In other embodiments, L of the heterocyclic 2-[(phosphinyl)aminyl]imine transition metal compound complexes having Structure HCPAITMC 1 can have Structure 1L; alternatively, Structure 2L; alternatively, Structure 3L; alternatively, Structure 4L; alternatively, Structure 5L; or alternatively, Structure 6L.

TABLE 1

| | |
|---|---|
| $-(CR^{L1}R^{L2})_m-$ | Structure 1L |
| $-CR^{L3}R^{L4}-CR^{L5}R^{L6}-$ | Structure 2L |
| $-CR^{L3}R^{L4}-CR^{L7}R^{L8}-CR^{L5}R^{L6}-$ | Structure 3L |
| $-CR^{L11}=CR^{L12}-$ | Structure 4L |
| 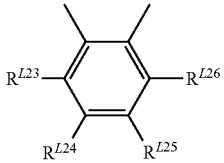 | Structure 5L |
| $-CR^{L31}R^{L32}-CR^{L33}=CR^{L34}-$ | Structure 6L |

Within the structures of Table 1, the undesignated valencies represent the points at which L attaches to T and the nitrogen atom, N, of the heterocyclic 2-[(phosphinyl)aminyl]imine transition metal compound complex having Structure HCPAITMC 1. Generally, m can be an integer ranging from 1 to 4. In further embodiments, m can be 2 or 3; alternatively, m can be 1; alternatively, m can be 2; alternatively, m can be 3; or alternatively, m can be 4. $R^{L1}$ and $R^{L2}$ of the linking group having Structure 1L, $R^{L3}$, $R^{L4}$, $R^{L5}$, and $R^{L6}$ of the linking group having Structure 2L, $R^{L3}$, $R^{L4}$, $R^{L5}$, $R^{L6}$, $R^{L7}$, and $R^{L8}$, of the linking group having Structure 3L, $R^{L11}$ and $R^{L12}$ of the linking group having Structure 4L, $R^{L23}$, $R^{L24}$, $R^{L25}$, and $R^{L26}$ of the linking group having Structure 5L, $R^{L31}$, $R^{L32}$, $R^{L33}$, and $R^{L34}$ of the linking group having Structure 6L independently can be a hydrogen or a non-hydrogen substituent group (any general or specific substituent group described herein); or alternatively, hydrogen. Non-hydrogen substituent groups (general and specific) are independently disclosed herein and can be utilized without limitation to further describe the linking group having Structure 1L, Structure 2L, Structure 3L, Structure 4L, Structure 5L, and/or Structure 6L. In an embodiment, L can be a methylene group (—$CH_2$—), an eth-1,2-ylene group (—$CH_2CH_2$—), an ethen-1,2-ylene group (—CH═CH—), a prop-1,3-ylene group (—$CH_2CH_2CH_2$—), a 1-methylethen-1,2-ylene group (—C($CH_3$)═CH—), a 1-methylprop-1,3-ylene group (—$CH_2CH_2CH(CH_3)$—), a 1,1-dimethylprop-1,3-ylene group (—$CH_2CH_2C(CH_3)_2$—), a but-1,4-ylene group (—$CH_2CH_2CH_2CH_2$—), or a phen-1,2-ylene group. In some non-limiting embodiments, L can be an eth-1,2-ylene group (—$CH_2CH_2$—), a prop-1,3-ylene group (—$CH_2CH_2CH_2$—), a 1-methylethen-1,2-ylene group (—C($CH_3$)═CH—), a 1-methylprop-1,3 -ylene group (—$CH_2CH_2CH(CH_3)$—), or a 1,1-dimethylprop-1,3-ylene group (—$CH2CH_2C(CH_3)_2$—); alternatively, an eth-1,2-ylene group (—$CH_2CH_2$—), an ethen-1,2-ylene group (—CH═CH—), a prop-1,3-ylene group (—$CH_2CH_2CH_2$—), a but-1,4-ylene group (—$CH_2CH_2CH_2CH_2$—), or a phen-1,2-ylene group; alternatively, an eth-1,2-ylene group (—$CH_2CH_2$—) or a prop-1,3-ylene group (—$CH_2CH_2CH_2$—); alternatively, an ethen-1,2-ylene group (—CH═CH—) or a phen-1,2-ylene group. In other embodiments, L can be a methylene group (—$CH_2$—); alternatively, an eth-1,2-ylene group (—$CH_2CH_2$—); alternatively, an ethen-1,2-ylene group (—CH═CH—); alternatively, a prop-1,3-ylene group (—$CH_2CH_2CH_2$—); alternatively, a 1-methylethen-1,2-ylene group (—C($CH_3$)═CH—); alternatively, a 1-methylprop-1,3 -ylene group (—$CH_2CH_2CH(CH_3)$—); alternatively, a 1,1-dimethylprop-1,3-ylene group (—$CH_2CH_2C(CH_3)_2$—); alternatively, a but-1,4-ylene group (—$CH_2CH_2CH_2CH_2$—); or alternatively, a phen-1,2-ylene group. In an embodiment, L can have a structure that can comprise at least one substituent located on the carbon atom attached to the nitrogen atom of the heterocyclic ring of the heterocyclic 2-[(phosphinyl)aminyl]imine transition metal compound complex; alternatively, can comprise only one substituent located on the carbon atom attached to the nitrogen atom of the heterocyclic ring of the heterocyclic 2-[(phosphinyl)aminyl]imine transition metal compound complex; or alternatively, can comprise two substituents located on the carbon atom attached to the nitrogen atom of the heterocyclic ring of the heterocyclic 2-[(phosphinyl) aminyl]imine transition metal compound complex. In another embodiment, L can have a structure that can consist of one substituent located on the carbon atom attached to the nitrogen atom of the heterocyclic ring of the heterocyclic 2-[(phosphinyl)aminyl]imine transition metal compound complex; or alternatively, can consist of two substituents located on the carbon atom attached to the nitrogen atom of the heterocyclic ring of the heterocyclic 2-[(phosphinyl) aminyl]imine transition metal compound complex.

Generally, $R^{11}$ of the heterocyclic 2-[(phosphinyl)aminyl] imine transition metal compound complexes having Structure HCPAITMC 2, Structure HCPAITMC 3, Structure HCPAITMC 5, Structure HCPAITMC 7, Structure HCPAITMC 8, and/or Structure HCPAITMC 10 can be hydrogen or an organyl group; alternatively, hydrogen or an organyl group consisting essentially of inert functional groups; alternatively, hydrogen or a hydrocarbyl group; alternatively, an organyl group; alternatively, an organyl group consisting essentially of inert functional groups; alternatively, a hydrocarbyl group; or alternatively, hydrogen. In an embodiment, the organyl group which can be utilized as $R^{11}$ can be a $C_1$ to $C_{20}$, a $C_1$ to $C_{15}$, a $C_1$ to $C_{10}$, or a $C_1$ to $C_5$ organyl group. In an embodiment, the organyl group consisting essentially of inert functional groups which can be utilized as $R^{11}$ can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, the hydrocarbyl group which can be utilized as $R^{11}$ can be a $C_1$ to $C_{20}$, a $C_1$ to $C_{15}$, a $C_1$ to $C_{10}$, or a $C_1$ to $C_5$ hydrocarbyl group.

In an embodiment, $R^{11}$ of the heterocyclic 2-[(phosphinyl)aminyl]imine transition metal compound complexes having Structure HCPAITMC 2, Structure HCPAITMC 3, Structure HCPAITMC 5, Structure HCPAITMC 7, Structure HCPAITMC 8, and/or Structure HCPAITMC 10, can be hydrogen, an alkyl group, or a substituted alkyl group; alternatively, hydrogen or an alkyl group; alternatively, hydrogen or a substituted alkyl group; alternatively, an alkyl group; alternatively, a substituted alkyl group; or alternatively, hydrogen. In any aspect or embodiment disclosed herein, the alkyl group which can be utilized as $R^{11}$ can be a $C_1$ to $C_{20}$, a $C_1$ to $C_{10}$, or a $C_1$ to $C_5$ alkyl group. In any aspect or embodiment disclosed herein, the substituted alkyl group which can be utilized as $R^{11}$ can be a $C_1$ to $C_{20}$, a $C_1$ to $C_{10}$, or a $C_1$ to $C_5$ substituted alkyl group. In an embodiment, $R^{11}$ can be a methyl group, an ethyl group, a propyl group, a butyl group, a pentyl group, a hexyl group, a heptyl group, or an octyl group. In some embodiments, $R^{11}$ can be a methyl group, an ethyl group, an n-propyl (1-propyl) group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, an n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the alkyl groups which can be utilized as $R^{11}$ can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups (general or specific) can be utilized without limitation to further describe a substituted alkyl group which can be utilized as $R^{11}$.

Generally, $R^{12}$, $R^{13}$, and $R^{14}$ of the heterocyclic 2-[(phosphinyl)aminyl]imine transition metal compound complexes having Structure HCPAITMC 2, Structure HCPAITMC 3, and/or Structure HCPAITMC 5 which have an $R^{12}$, $R^{13}$, and/or $R^{14}$ group, $R^{21}$ of the heterocyclic 2-[(phosphinyl) aminyl]imine transition metal compound complexes having Structure HCPAITMC 4, Structure HCPAITMC 6, Structure HCPAITMC 9, and/or Structure HCPAITMC 11, and $R^{22}$, $R^{23}$, and $R^{24}$ of the heterocyclic 2-[(phosphinyl)aminyl] imine transition metal compound complexes having Structure HCPAITMC 4 and/or Structure HCPAITMC 6 independently can be hydrogen or an organyl group; alternatively, hydrogen or an organyl group consisting essentially of inert functional groups; alternatively, hydrogen or a hydrocarbyl group; alternatively an organyl group; alternatively, an organyl group consisting essentially of inert functional groups; alternatively, a hydrocarbyl group; or alternatively, hydrogen. In an embodiment, each organyl group which can be utilized for $R^{12}$, $R^{13}$, $R^{14}$, $R^{21}$, $R^{22}$, $R^{23}$, and/or $R^{24}$ independently can be a $C_1$ to $C_{20}$, a $C_1$ to $C_{15}$, a $C_1$ to $C_{10}$, or a $C_1$ to $C_5$ organyl group. In an embodiment, each organyl group consisting essentially of inert functional groups which can be utilized for $R^{12}$, $R^{13}$, $R^{14}$, $R^{21}$, $R^{22}$, $R^{23}$, and/or $R^{24}$ independently can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, each hydrocarbyl group which can be utilized for $R^{12}$, $R^{13}$, $R^{14}$, $R^{21}$, $R^{22}$, $R^{23}$, and $R^{24}$ independently can be a $C_1$ to $C_{20}$, a $C_1$ to $C_{15}$, a $C_1$ to $C_{10}$, or a $C_1$ to $C_5$ hydrocarbyl group.

In an embodiment, $R^{12}$, $R^{13}$, and $R^{14}$ of the heterocyclic 2-[(phosphinyl)aminyl]imine transition metal compound complexes having Structure HCPAITMC 2, Structure HCPAITMC 3, and/or Structure HCPAITMC 5 which have an $R^{12}$, $R^{13}$, and/or $R^{14}$ group, $R^{21}$ of the heterocyclic 2-[(phosphinyl)aminyl]imine transition metal compound complexes having Structure HCPAITMC 4, Structure HCPAITMC 6, Structure HCPAITMC 9, and/or Structure HCPAITMC 11, and $R^{22}$, $R^{23}$, and $R^{24}$ of the heterocyclic 2-[(phosphinyl)aminyl]imine transition metal compound complexes having Structure HCPAITMC 4 and/or Structure HCPAITMC 6 independently can be hydrogen, an alkyl group, or a substituted alkyl group; alternatively, hydrogen or an alkyl group; alternatively, hydrogen or a substituted alkyl group; alternatively, an alkyl group; alternatively, a substituted alkyl group; or alternatively, hydrogen. In any embodiment or aspect where the heterocyclic 2-[(phosphinyl)aminyl]imine transition metal compound complex has multiple substituents, one or more of the substituents can be the same or all of the substituents can be different; alternatively, one or more of the substituents can be the same; or alternatively, all of the substituents can be different. In any aspect or embodiment disclosed herein, each alkyl group which can be utilized as $R^{12}$, $R^{13}$, $R^{14}$, $R^{21}$, $R^{22}$, $R^{23}$ and/or $R^{24}$ independently can be a $C_1$ to $C_{20}$, a $C_1$ to $C_{10}$, or a $C_1$ to $C_5$ alkyl group. In any aspect or embodiment disclosed herein, each substituted alkyl group which can be utilized as $R^{12}$, $R^{13}$, $R^{14}$, $R^{21}$, $R^{22}$, $R^{23}$, and/or $R^{24}$ independently can be a $C_1$ to $C_{20}$, a $C_1$ to $C_{10}$, or a $C_1$ to $C_5$ substituted alkyl group. In an embodiment, each alkyl group which can be utilized as $R^{12}$, $R^{13}$, $R^{14}$, $R^{21}$, $R^{22}$, $R^{23}$, and/or $R^{24}$ independently can be a methyl group, an ethyl group, a propyl group, a butyl group, a pentyl group, a hexyl group, a heptyl group, or an octyl group; alternatively a methyl group, an ethyl group, an n-propyl (1-propyl) group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, an n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the specific alkyl groups which can be utilized as $R^{12}$, $R^{13}$, $R^{14}$, $R^{21}$, $R^{22}$, $R^{23}$, and/or $R^{24}$ independently can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as $R^{12}$, $R^{13}$, $R^{14}$, $R^{21}$, $R^{22}$, $R^{23}$, and/or $R^{24}$.

In a particular embodiment of the heterocyclic 2-[(phosphinyl)aminyl]imine transition metal compound complexes having Structure HCPAITMC 2, Structure HCPAITMC 3, and/or Structure HCPAITMC 5, $R^{11}$ can be any non-hydrogen substituent group described herein for $R^{11}$, $R^{13}$ can be hydrogen, and $R^{12}$ and/or $R^{14}$ can be hydrogen for the structures which have an $R^{12}$ and/or $R^{14}$ group. In another particular embodiment of the heterocyclic 2-[(phosphinyl)aminyl]imine transition metal compound complexes having Structure HCPAITMC 4, and/or Structure HCPAITMC 6, $R^{21}$ can be any non-hydrogen substituent group described herein for $R^{21}$, and $R^{22}$, $R^{23}$, and $R^{24}$ can be hydrogen.

In an embodiment, $R^{11}$ or $R^{12}$ and $R^{13}$ or $R^{14}$ of the heterocyclic 2-[(phosphinyl)aminyl]imine transition metal compound complexes having Structure HCPAITMC 2, and/or Structure HCPAITMC 5, having non-hydrogen $R^{11}$ or $R^{12}$ and $R^{13}$ or $R^{14}$ groups (regardless of particular type of group—organyl, organyl consisting of inert functional groups, or hydrocarbyl group, including any species, sub-species, or individuals contained and/or described herein) can be joined to form a ring or ring system. In some embodiments, $R^{11}$ and $R^{13}$ of the heterocyclic 2-[(phosphinyl)aminyl]imine transition metal compound complexes having Structure HCPAITMC 3 having non-hydrogen $R^{11}$ and $R^{13}$ groups (regardless of particular type of group—organyl, organyl consisting of inert functional groups, or hydrocarbyl group, including any species, sub-species, or individuals contained and/or described herein) can be joined to form a ring or ring system. In other embodiments $R^{21}$ and $R^{22}$, $R^{22}$ and $R^{23}$, and/or $R^{23}$ and $R^{24}$ of the heterocyclic 2-[(phosphinyl)aminyl]imine transition metal compound complexes having Structure HCPAITMC 4, and/or Structure HCPAITMC 6 having non-hydrogen $R^{21}$ and $R^{22}$ groups, non-hydrogen $R^{22}$ and $R^{23}$ groups, or non-hydrogen $R^{23}$ and $R^{24}$ groups (regardless of particular type of group—organyl, organyl consisting of inert functional groups, or hydrocarbyl group, including any species, sub-species, or individuals contained and/or described herein) can be joined to form a ring or ring system.

The transition metal compound of the heterocyclic 2-[(phosphinyl)aminyl]imine transition metal compound complexes described herein can have the formula $MX_p$ where, M represent the transition metal, X represents a monoanionic ligand, and p represents the number of monoanionic ligands (and the oxidation state of the transition metal in the transition metal compound). The transition metal (M), the monoanionic ligand (X), and p are independent elements of the transition metal compound that are independently described herein. The independent descriptions of the transition metal, the monoanionic ligand (X), and p can be utilized without limitation, and in any combination, to further describe the transition metal compound ($MX_p$) of the heterocyclic 2-[(phosphinyl)aminyl]imine transition metal compound complexes.

Generally, the transition metal atom of the transition metal compound, $MX_p$ can be any transition metal atom. In an embodiment, the transition metal atom of the transition metal compound can comprise, or consist essentially of, a Group 3-12, a Group 4-10, a Group 6-9, or a Group 7-8 transition metal. In some embodiments, the transition metal atom of the transition metal compound can comprise, or consist essentially of, a Group 4 transition metal; alternatively, a Group 5 transition metal; alternatively, a Group 6 transition metal; alternatively, a Group 7 transition metal; alternatively, a Group 8 transition metal; alternatively, a Group 9 transition metal; or alternatively, a Group 10 transition metal. In an embodiment, the transition metal atom of the transition metal compound can comprise, or can consist essentially of, titanium, zirconium, hafnium, vanadium, niobium, tantalum, chromium, molybdenum, tungsten, manganese, iron, cobalt, nickel, palladium, platinum, copper, or zinc; alternatively, titanium, zirconium, vanadium, chromium, molybdenum, tungsten, iron, cobalt, nickel, palladium, or platinum; alternatively, chromium, iron, cobalt, or nickel; alternatively, titanium, zirconium, or hafnium; alternatively, vanadium or niobium; alternatively, chromium, molybdenum, or tungsten; alternatively, iron or cobalt; or alternatively, nickel, palladium, platinum, copper, or zinc. In other embodiments, the transition metal atom can comprise titanium; alternatively, zirconium; alternatively, hafnium; alternatively, vanadium; alternatively, niobium; alternatively, tantalum; alternatively, chromium; alternatively, molybdenum; alternatively, tungsten; alternatively, manganese; alternatively, iron; alternatively, cobalt; alternatively, nickel; alternatively, palladium; alternatively, platinum; alternatively, copper; or alternatively, zinc.

Generally, the transition metal atom of the transition metal compound, $MX_p$, can have any positive oxidation state available to the transition metal atom. In an embodiment, the transition metal atom can have an oxidation state of from +2 to +6; alternatively, from +2 to +4; or alternatively, from +2 to +3. In some embodiments, the transition metal atom of the transition metal compound, $MX_p$, can have an oxidation state of +1; alternatively, +2; alternatively, +3; or alternatively, +4.

The monoanion, X, of the transition metal compound can be any monoanion. In an embodiment, the monoanion, X, can be a halide, a carboxylate, a β-diketonate, a hydrocarboxide, a nitrate, or a chlorate. In some embodiments, the monoanion, X, can be a halide, a carboxylate, a β-diketonate, or a hydrocarboxide; alternatively, a halide, a carboxylate, or a β-diketonate. In any aspect or embodiment, the hydrocarboxide can be an alkoxide, an aryloxide, or an aralkoxide. Generally, hydrocarboxides (and subdivisions of hydrocarboxides) are the anion analogues of the hydrocarboxy group. In other embodiments, the monoanion, X, can be a halide, a carboxylate, a β-diketonate, or an alkoxide; alternatively, a halide or a carboxylate; or alternatively, a halide or a β-diketonate. In other embodiments, the monoanion, X, can be a halide; alternatively, a carboxylate; alternatively, a β-diketonate; alternatively, a hydrocarboxide; alternatively, an alkoxide; or alternatively, an aryloxide. Generally, the number, p, of monoanions can equal the oxidation state of the metal atom. In an embodiment, the number, p, of monoanions, X, can be an integer from 1 to 6; alternatively, an integer from 2 to 6; alternatively, an integer from 2 to 4; alternatively, an integer from 2 to 3; alternatively, 1; alternatively, 2; alternatively, 3; or alternatively, 4.

Generally, each halide monoanion, X, of the transition metal compound independently can be fluorine, chlorine, bromine, or iodine; or alternatively, chlorine, bromine, or iodine. In an embodiment, each halide monoanion, X, of the transition metal compound can be chlorine; alternatively, bromine; or alternatively, iodine.

Generally, each carboxylate monoanion of the transition metal compound independently can be a $C_1$ to $C_{20}$ carboxylate; or alternatively, a $C_1$ to $C_{10}$ carboxylate. In an embodiment, each carboxylate monoanion of the transition metal compound independently can be acetate, a propionate, a butyrate, a pentanoate, a hexanoate, a heptanoate, an octanoate, a nonanoate, a decanoate, an undecanoate, or a dodecanoate; or alternatively, a pentanoate, a hexanoate, a heptanoate, an octanoate, a nonanoate, a decanoate, an undecanoate, or a dodecanoate. In some embodiments, each carboxylate monoanion of the transition metal compound independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, valerate (n-pentanoate), n-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate); or alternatively, 2-ethylhexanoate. In some embodiments, the carboxylate monoanion of the transition metal compound can be triflate (trifluoroacetate).

Generally, each β-diketonate monoanion of the transition metal compound independently can be any $C_1$ to $C_{20}$ β-diketonate; or alternatively, any $C_1$ to $C_{10}$ β-diketonate. In an embodiment, each β-diketonate monoanion of the transition metal compound independently can be acetylacetonate (i.e., 2,4-pentanedionate), hexafluoroacetylacetone (i.e., 1,1,1,5,5,5-hexafluoro-2,4-pentanedionate), or benzoylacetonate); alternatively, acetylacetonate; alternatively, hexafluoroacetylacetone; or alternatively, benzoylacetonate.

Generally, each hydrocarboxide monoanion of the transition metal compound independently can be any $C_1$ to $C_{20}$ hydrocarboxide; or alternatively, any $C_1$ to $C_{10}$ hydrocarboxide. In an embodiment, each hydrocarboxide monoanion of the transition metal compound independently can be a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide. In an embodiment, each alkoxide monoanion of the transition metal compound independently can be methoxide, ethoxide, a propoxide, or a butoxide. In some embodiments, each alkoxide monoanion of the transition metal compound independently can be methoxide, ethoxide, isopropoxide, or tert-butoxide; alternatively, methoxide; alternatively, ethoxide; alternatively, iso-propoxide; or alternatively, tert-butoxide. In an aspect, the aryloxide can be phenoxide.

In a particular aspect, the transition metal compound of the heterocyclic 2-[(phosphinyl)aminyl]imine transition metal compound complexes can be a chromium compound having the formula $CrX_p$. In such instances $CrX_p$ can replace $MX_p$ in any heterocyclic 2-[(phosphinyl)aminyl]imine transition metal compound complex presented herein and the heterocyclic 2-[(phosphinyl)aminyl]imine transition metal compound complexes can be referred to as heterocyclic 2-[(phosphinyl)aminyl]imine chromium compound complexes. Generally, the chromium compound of the heterocyclic 2-[(phosphinyl)aminyl]imine transition metal compound complexes described herein has the formula $CrX_p$ where X represents a monoanionic ligand, and p represents the number of monoanionic ligands (and the oxidation state of the chromium in the chromium compound). The monoanionic ligand (X) and p are independent elements of the chromium compound and are independently described herein. The independent descriptions of the monoanionic ligand (X) and p can be utilized without limitation, and in any combination, to further describe the chromium compound of the heterocyclic 2-[(phosphinyl)aminyl]imine transition metal compound complexes.

In a non-limiting embodiment, the chromium compound of any of the heterocyclic 2-[(phosphinyl)aminyl]imine transition metal compound complexes described herein can comprise, can consist essentially of, or can consist of, a chromium(II) halide, a chromium(III) halide, a chromium (II) carboxylate, a chromium(III) carboxylate, a chromium (II) β-diketonate, or a chromium(III) β-diketonate. In some non-limiting embodiments, the chromium compound of any of the heterocyclic 2-[(phosphinyl)aminyl]imine transition metal compound complexes described herein can comprise, can consist essentially of, or can consist of, a chromium(II) halide, a chromium(II) carboxylate, or a chromium(II) β-diketonate; or alternatively, a chromium(III) halide, a chromium(III) carboxylate, or a chromium(III) β-diketonate. In other non-limiting embodiments, the chromium compound of any of the heterocyclic 2-[(phosphinyl)aminyl]imine transition metal compound complexes described herein can comprise, can consist essentially of, or can consist of, a chromium(II) halide; alternatively, a chromium (III) halide; alternatively, a chromium (II) carboxylate; alternatively, a chromium(III) carboxylate; alternatively, a chromium(II) β-diketonate; or alternatively, a chromium(III) β-diketonate.

In a non-limiting embodiment, the chromium compound of any of the heterocyclic 2-[(phosphinyl)aminyl]imine transition metal compound complexes described herein can comprise, can consist essentially of, or can consist of, chromium(II) chloride, chromium(III) chloride, chromium (II) fluoride, chromium(III) fluoride, chromium(II) bromide, chromium(III) bromide, chromium(II) iodide, chromium (III) iodide, chromium(II) acetate, chromium(III) acetate, chromium(II) 2-ethylhexanoate, chromium(III) 2-ethylhexanoate, chromium(II) triflate, chromium(III) triflate, chromium(II) nitrate, chromium(III) nitrate, chromium(II) acetylacetonate, chromium(III) acetylacetonate, chromium (II) hexafluoracetylacetonate, chromium(III) hexafluoracetylacetonate, chromium(II) benzoylacetonate, or chromium(III) benzoylacetonate. In some non-limiting embodiments, the chromium compound of any of the heterocyclic 2-[(phosphinyl)aminyl]imine transition metal compound complexes described herein can comprise, can consist essentially of, or can consist of, chromium(III) chloride, chromium(III) fluoride, chromium(III) bromide, chromium(III) iodide, chromium(III) acetate, chromium(III) 2-ethylhexanoate, chromium(III) triflate, chromium(III) nitrate, chromium(III) acetylacetonate, chromium(III) hexafluoracetylacetonate, or chromium(III) benzoylacetonate. In further embodiments, the chromium compound of any of the heterocyclic 2-[(phosphinyl)aminyl]imine transition metal compound complexes described herein can be chromium(III) chloride or chromium(III) acetylacetonate; alternatively, chromium(III) chloride; or alternatively, chromium(III) acetylacetonate.

Generally, the neutral ligand, Q, of any of the heterocyclic 2-[(phosphinyl)aminyl]imine transition metal compound complexes described herein, if present, independently can be any neutral ligand that can form an isolatable compound with the heterocyclic 2-[(phosphinyl)aminyl]imine transition metal compound complex. In an aspect, each neutral ligand independently can be a nitrile, an ether, or an amine; alternatively, a nitrile or an ether; alternatively, a nitrile; or alternatively, an ether. The number of neutral ligands, q, can be any number that can form an isolatable compound with the heterocyclic 2-[(phosphinyl)aminyl]imine transition metal compound complex. In an embodiment, the number of neutral ligands, q, can range from 0 to 6, or from 0 to 3. In other embodiments, the number of neutral ligands, q, can be 0; alternatively, 1; alternatively, 2; or alternatively, 3.

Generally, each neutral nitrile ligand can be a $C_2$ to $C_{20}$ nitrile; or alternatively, a $C_2$ to $C_{10}$ nitrile. In an embodiment, each neutral nitrile ligand independently can be a $C_2$ to $C_{20}$ aliphatic nitrile, a $C_7$ to $C_{20}$ aromatic nitrile, a $C_8$ to $C_{20}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_8$ to $C_{20}$ aralkane nitrile. In some embodiments, each neutral nitrile ligand independently can be a $C_2$ to $C_{10}$ aliphatic nitrile, a $C_7$ to $C_{10}$ aromatic nitrile, a $C_8$ to $C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_8$ to $C_{10}$ aralkane nitrile. In an embodiment, each aliphatic nitrile independently can be acetonitrile, propionitrile, butyronitrile, or any combination thereof; alternatively, acetonitrile; alternatively, propionitrile; or alternatively, butyronitrile. In an embodiment, each aromatic nitrile independently can be benzonitrile, 2-methylbenzonitrile, 3-methylbenzonitrile, 4-methylbenzonitrile, 2-ethylbenzonitrile, 3-ethylbenzonitrile, 4-ethylbenzonitrile, or any combination thereof; alternatively, benzonitrile; alternatively, 2-methylbenzonitrile; alternatively, 3-methylbenzonitrile; alternatively, 4-methylbenzonitrile; alternatively, 2-ethylbenzonitrile; alternatively, 3-ethylbenzonitrile; or alternatively, 4-ethylbenzonitrile.

Generally, each neutral ether ligand can be a $C_2$ to $C_{40}$ ether; alternatively, a $C_2$ to $C_{30}$ ether; or alternatively, a $C_2$ to $C_{20}$ ether. In an embodiment, each neutral ether ligand independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some embodiments, each neutral ether ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other embodiments, each neutral ether ligand independently can be a $C_2$ to $C_{20}$ aliphatic ether, a $C_3$ to $C_{20}$ aliphatic cyclic ether, a $C_4$ to $C_{20}$ aromatic cyclic ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some embodiments, each ether ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, dibenzofuran, diphenyl ether, a ditolyl ether, or any combination thereof; alternatively, dimethyl ether, diethyl ether, a dipropyl ether, a dibutyl ether, methyl ethyl ether, a methyl propyl ether, a methyl butyl ether, or any combination thereof; alternatively, tetrahydrofuran, a dihydrofuran, 1,3-dioxolane, tetrahydropyran, a dihydropyran, a pyran, a dioxane, or any combination thereof; alternatively, furan, benzofuran, isobenzofuran, dibenzofuran, or any combination thereof; alternatively, diphenyl ether, a ditolyl ether, or any combination thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, dibenzofuran; alternatively, diphenyl ether; or alternatively, a ditolyl ether.

Generally, the organoaluminum compound utilized in the catalyst systems disclosed herein can be any organoaluminum compound which in combination with the heterocyclic 2-[(phosphinyl)aminyl]imine transition metal compound complex can catalyze the formation of an oligomer product. In an aspect, the organoaluminum compound can be an aluminoxane, an alkylaluminum compound, or any combination thereof; alternatively, an aluminoxane; or alternatively, an alkylaluminum compound. In an embodiment, the alkylaluminum compound can be a trialkylaluminum, an alkylaluminum halide, an alkylaluminum alkoxide, or any combination thereof. In some embodiments, the alkylaluminum compound can be a trialkylaluminum, an alkylaluminum halide, or any combination thereof; alternatively, a trialkylaluminum, an alkylaluminum alkoxide, or any combination thereof; or alternatively, a trialkylaluminum. In other embodiments, the alkylaluminum compound can be a trialkylaluminum; alternatively, an alkylaluminum halide; or alternatively, an alkylaluminum alkoxide.

In a non-limiting embodiment, the aluminoxane can have a repeating unit characterized by Formula I:

Formula I wherein R' is a linear or branched alkyl group. Alkyl groups suitable for use within the aluminoxane comprising Formula I are independently described herein and can be utilized without limitation to further describe the aluminoxanes having Formula I. Generally, n of Formula I can be greater than 1; or alternatively, greater than 2. In an embodiment, n can range from 2 to 15; or alternatively, range from 3 to 10.

In an aspect, each alkyl group of any organoaluminum compound disclosed herein (trialkylaluminum, alkylaluminum halide, alkylaluminum alkoxide, or aluminoxane, among others) independently can be, comprise, or consist essentially of, a $C_1$ to $C_{20}$, a $C_1$ to $C_{10}$, or a $C_1$ to $C_6$ alkyl group. In an embodiment, each alkyl group of any alkylaluminum compound disclosed herein independently can be, comprise, or consist essentially of, a methyl group, an ethyl group, a propyl group, a butyl group, a pentyl group, a hexyl group, a heptyl group, or an octyl group; alternatively, a methyl group, an ethyl group, a butyl group, a hexyl group, or an octyl group. In some embodiments, each alkyl group of any alkylaluminum compound disclosed herein independently can be, comprise, or consist essentially of, a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, each halide of any alkylaluminum halide disclosed herein can be, comprise, or consist essentially of, chloride, bromide, or iodide. In some embodiments, each halide of any alkylaluminum halide disclosed herein can be, comprise, or consist essentially of, chloride or bromide; or alternatively, chloride.

In an aspect, each alkoxide group of any alkylaluminum alkoxide disclosed herein independently can be, comprise, or consist essentially of, a $C_1$ to $C_{20}$, a $C_1$ to $C_{10}$, or a $C_1$ to $C_6$ alkoxy group. In an embodiment, each alkoxide group of any alkylaluminum alkoxide disclosed herein independently can be, comprise, or consist essentially of, a methoxy group, an ethoxy group, a propoxy group, a butoxy group, a pentoxy group, a hexoxy group, a heptoxy group, or an octoxy group; alternatively, a methoxy group, an ethoxy group, a butoxy group, a hexoxy group, or an octoxy group. In some embodiments, each alkoxide group of any alkylaluminum alkoxide disclosed herein independently can be, comprise, or consist essentially of, a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting embodiment, the trialkylaluminum compound can be, comprise, or consist essentially of, trimethylaluminum, triethylaluminum, tripropylaluminum, tributylaluminum, trihexylaluminum, trioctylaluminum, or mixtures thereof. In some non-limiting embodiments, the trialkylaluminum compound can be, comprise, or consist essentially of, trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting embodiments, the trialkylaluminum compound can be, comprise, or consist essentially of, trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting embodiment, the alkylaluminum halide can be, comprise, or consist essentially of, diethylaluminum chloride, diethylaluminum bromide, ethylaluminum dichloride, ethylaluminum sesquichloride, or mixtures thereof. In some non-limiting embodiments, the alkylaluminum halide can be, comprise, or consist essentially of, diethylaluminum chloride, ethylaluminum dichloride, ethylaluminum sesquichloride, or mixtures thereof. In other non-limiting embodiments, the alkylaluminum halide can be, comprise, or consist essentially of, diethylaluminum chloride; alternatively, diethylaluminum bromide; alternatively, ethylaluminum dichloride; or alternatively, ethylaluminum sesquichloride.

In a non-limiting embodiment, the aluminoxane can be, comprise, or consist essentially of, methylaluminoxane (MAO), ethylaluminoxane, a modified methylaluminoxane (MMAO), n-propylaluminoxane, iso-propylaluminoxane, n-butylaluminoxane, sec-butylaluminoxane, iso-butylaluminoxane, t-butylaluminoxane, 1-pentyl-aluminoxane, 2-pentylaluminoxane, 3-pentyl-aluminoxane, iso-pentylaluminoxane, neopentylaluminoxane, or mixtures thereof. In some non-limiting embodiments, the aluminoxane can be, comprise, or consist essentially of, methylaluminoxane (MAO), a modified methylaluminoxane (MMAO), isobutylaluminoxane, t-butylaluminoxane, or mixtures thereof. In other non-limiting embodiments, the aluminoxane can be, comprise, or consist essentially of, methylaluminoxane (MAO); alternatively, ethylaluminoxane; alternatively, a modified methylaluminoxane (MMAO); alternatively, n-propylaluminoxane; alternatively, iso-propylaluminoxane; alternatively, n-butylaluminoxane; alternatively, sec-butylaluminoxane; alternatively, iso-butylaluminoxane; alternatively, t-butylaluminoxane; alternatively, 1-pentylaluminoxane; alternatively, 2-pentylaluminoxane; alternatively, 3-pentylaluminoxane; alternatively, iso-pentylaluminoxane; or alternatively, neopentylaluminoxane.

In an aspect, the organoaluminum compound and the heterocyclic 2-[(phosphinyl)aminyl]imine transition metal compound complex can be combined in any ratio that can form an active catalyst system. In an embodiment, the catalyst systems can have a minimum aluminum of the organoaluminum compound (e.g., aluminoxane, among others) to transition metal (i.e., M) of the heterocyclic 2-[(phosphinyl)aminyl]imine transition metal compound complex molar ratio (i.e., minimum Al to M molar ratio) of 10:1, 50:1, 75:1, or 100:1. In other embodiments, the catalyst systems can have a maximum aluminum of the organoaluminum compound (e.g., aluminoxane, among others) to transition metal of the heterocyclic 2-[(phosphinyl)aminyl] imine transition metal compound complex molar ratio molar ratio (i.e., maximum Al to M molar ratio) of 5,000:1, 3,000:1, 2,000:1, 1,500:1, or 1,000:1. In an embodiment, the catalyst systems can have an Al to M molar ratio ranging from any minimum Al to M molar ratio disclosed herein to any maximum Al to M molar ratio disclosed herein. In a non-limiting embodiment, the Al to M molar ratio can range from 10:1 to 5,000:1, from 50:1 to 3,000:1, from 50:1 to 3,000:1, from 75:1 to 2,000:1, from 100:1 to 1,500:1, of from 100:1 to 1,000:1. Other Al to M molar ratio ranges that can be utilized are readily apparent to those skilled in the art with the aid of this disclosure. It should be noted that when a specific transition metal is used for the heterocyclic 2-[(phosphinyl)aminyl]imine transition metal compound complex (e.g., chromium, Cr), the specific metal can be utilized in place of the general transition metal in the minimum, maximum, and intermediate ranges for the Al to M molar ratios (e.g., Al to Cr molar ratios).

Generally, the catalyst systems can be prepared by contacting a heterocyclic 2-[(phosphinyl)aminyl]imine transition metal compound complex (any described herein) and an organoaluminum compound (any described herein) to form a catalyst system. In an embodiment, the catalyst systems can be prepared by: i) contacting the heterocyclic 2-[(phosphinyl)aminyl]imine transition metal compound complex (any described herein) and the organoaluminum compound (any described herein) to form a catalyst system mixture; and ii) aging the catalyst system mixture in a substantial absence of ethylene to form an aged catalyst system mixture. In a non-limiting embodiment, the substantial absence of ethylene can be a maximum molar ratio of ethylene to heterocyclic 2-[(phosphinyl)aminyl]imine transition metal compound complex of 5:1, 4:1, 3:1, 2:1, 1:1, 0.5:1, 0.25:1, or 0.1:1. In some non-limiting embodiments, the substantial absence of ethylene can be a maximum ethylene partial pressure 10 psig (69 kPa), 5 psig (34 kPa), 4 psig (28 kPa), 3 psig (21 kPa), 2 psig (14 kPa), 1 psig (7 kPa), or 0.5 psig (3.5 kPa). In some embodiments, the catalyst system can be formed in (or the catalyst system mixture can include) an organic liquid medium. Generally, the organic liquid medium can be selected from any organic reaction medium described herein. In an embodiment, the organic liquid medium can be the same as the organic reaction medium; or alternatively the organic liquid medium and the organic reaction medium can be different.

In an embodiment, the catalyst system mixture can be aged for a period of time. Typically, the minimum aging time can be 5 seconds, 10 seconds, 30 seconds, 1 minute, 5 minutes, 10 minutes, or 20 minutes; additionally or alternatively, the maximum aging time can be 48 hours, 36 hours, 24 hours, 18 hours, 12 hours, 6 hours, 4 hours, or 2 hours. Generally, the aging time can be in a range from any minimum time disclosed herein to any maximum time disclosed herein. Accordingly, suitable non-limiting ranges for the aging time can include from 5 seconds to 48 hours, from 10 seconds to 36 hours, from 30 seconds to 24 hours, from 1 minute to 18 hours, from 5 minutes to 6 hours, from 10 minutes to 4 hours, or from 20 minutes to 2 hours. Other appropriate ranges for the aging time are readily apparent from this disclosure.

In further embodiments, the catalyst system mixture can be aged at any suitable temperature, ranging from subambient temperatures, to ambient temperature (15° C. to 35° C. as defined herein), to elevated temperatures. While not limited thereto, the catalyst system mixture can be aged at a temperature in a range from 0° C. to 100° C., from 10° C. to 75° C., from 15° C. to 60° C., or from 20° C. to 40° C. In these and other embodiments, these temperature ranges also are meant to encompass circumstances where the catalyst system mixture can be aged at a series of different temperatures, instead of at a single fixed temperature, wherein the different temperatures comprise values within the ranges disclosed herein.

In an aspect, the present disclosure includes processes comprising contacting (or alternatively, introducing into a reaction zone): i) ethylene; ii) a catalyst system comprising (a) a heterocyclic 2-[(phosphinyl)aminyl]imine transition metal compound complex, and (b) an organoaluminum compound; and iii) optionally hydrogen to form an oligomer product. In another aspect, the present application includes processes comprising contacting (or alternatively, introducing into a reaction zone): i) ethylene; ii) a catalyst system comprising (a) a heterocyclic 2-[(phosphinyl)aminyl]imine transition metal compound complex, and (b) an organoaluminum compound; iii) an organic reaction medium; and iv) optionally hydrogen to form the oligomer product. In an embodiment, the processes can utilize a catalyst system mixture and can further comprise forming a catalyst system mixture comprising the catalyst system components and optionally aging the catalyst system mixture as described herein and contacting the catalyst system mixture or the aged catalyst system mixture with ethylene, the organoaluminum compound, optional organic reaction medium, and optional hydrogen. Thus in an aspect, the processes described herein can further comprise the steps of contacting a heterocyclic 2-[(phosphinyl)aminyl]imine transition metal compound complex (any described herein), an organoaluminum compound (any described herein), and optionally an organic liquid medium (any described herein) to form a catalyst system (or alternatively, a catalyst system mixture): or alternatively further comprise 1) contacting a heterocyclic 2-[(phosphinyl)aminyl]imine transition metal compound complex (any described herein), an organoaluminum compound (any described herein), and optionally an organic liquid medium (any described herein) to form a catalyst system (or alternatively, a catalyst system mixture), and ii) aging the catalyst system mixture in a substantial absence of ethylene to form an aged catalyst system mixture. In any aspect or embodiment, the oligomer product can be formed in a reaction zone. In any embodiment or aspect in which the oligomer product is formed in a reaction zone, the process can further comprise removing a reaction zone effluent comprising the oligomer product from the reaction zone and optionally isolating one or more oligomer products from the reaction zone effluent. The heterocyclic 2-[(phosphinyl) aminyl]imine transition metal compound complex, the organoaluminum compound, the organic liquid medium, the organic reaction medium, the conditions under which the oligomer product can be formed (or alternatively, the conditions under which the reaction zone can operate), and features of the oligomer product (among other composition, mixture, oligomer product, and process features) are independently described herein and can be utilized, without limitation, and in any combination, to further describe the processes described herein.

In an embodiment, the processes described herein can be a batch process or a continuous process. In any aspect or embodiment, the reaction zone utilized in the processes described herein can comprise any reactor which can oligomerize, trimerize, tetramerize, or trimerize and tetramerize ethylene to an oligomer product. In some embodiments, the reaction zone can comprise one or more reactors. In any aspect or embodiment, the reaction zone can comprise a stirred tank reactor, a plug flow reactor, or any combination thereof; alternatively, a stirred tank reactor; or alternatively, a plug flow reactor. In any aspect or embodiment, the reaction zone of any process, system, or reaction system described herein can comprise an autoclave reactor, a continuous stirred tank reactor, a loop reactor, a gas phase reactor, a solution reactor, a tubular reactor, a recycle reactor, a bubble reactor, or any combination thereof; alternatively, an autoclave reactor; alternatively, a stirred tank reactor; alternatively, a loop reactor; alternatively, a gas phase reactor; alternatively, a solution reactor; alternatively, a tubular reactor; alternatively, a recycle reactor; or alternatively, a bubble reactor. In some aspects and embodiments, the reaction zone can comprise multiple reactors; or alternatively, a single reactor. When multiple reactors are present, each of the reactors can be the same or different types of reactors. The reaction zone can comprise single or multiple reactors of any type disclosed herein operating in batch or continuous mode and/or in series or parallel. In a continuous process aspect or embodiment, the process can further comprise periodically or continuously introducing/feeding ethylene, a catalyst system, optionally organic reaction medium, and/or optionally hydrogen to the reaction zone and/or periodically or continuously removing a reaction zone effluent from the reaction zone.

In an embodiment, the heterocyclic 2-[(phosphinyl)aminyl]imine transition metal compound complexes can be utilized in a catalyst system in an ethylene oligomerization, trimerization, tetramerization, or trimerization and tetramerization process. Generally, the oligomer product that can be produced using the processes described herein can be formed at conditions (or alternatively, the reaction zone can have conditions) which can 1) facilitate oligomer product formation, 2) provide a desired oligomer product formation rate, 3) provide acceptable catalyst system productivity, 4) provide acceptable oligomer selectivity, and/or 5) provide acceptable polymer formation.

In an embodiment, the conditions under which the oligomer product can be formed (or alternatively, the reaction zone can operate) can include one or more of catalyst system component ratios, transition metal (e.g., chromium) concentration, pressure, ethylene partial pressure, ethylene concentration, presence of hydrogen (and its partial pressure and/or hydrogen to ethylene weight ratio), temperature, reaction time, single pass ethylene conversion, and catalyst system productivity. Catalyst system component ratios, transition metal (e.g., chromium) concentration, pressure, ethylene partial pressure, ethylene concentration, presence of hydrogen (and its partial pressure and/or hydrogen to ethylene weight ratio), temperature, reaction time, single pass ethylene conversion, and catalyst system productivity are independently described herein and these independent descriptions can be used without limitation and in any combination to describe the conditions at which the oligomer product can be formed (or alternatively, the conditions at which the reaction zone can operate).

In an embodiment, the oligomer product can be formed (or the reaction zone can operate) at a minimum reaction zone transition metal concentration of the heterocyclic 2-[(phosphinyl)aminyl]imine transition metal compound complex (i.e., minimum transition metal, M, concentration) of $1 \times 10^{-6}$ equivalents/liter, $1 \times 10^{-5}$ equivalents/liter, or $5 \times 10^{-4}$ equivalents/liter; additionally or alternatively, at a maximum reaction zone transition metal concentration of the heterocyclic 2-[(phosphinyl)aminyl]imine transition metal compound complex (i.e., maximum transition metal, M, concentration) of 1 equivalent/liter, 0.5 equivalents/liter, or 0.1 equivalents/liter. In an embodiment, the oligomer product can be formed (or the reaction zone can operate) at a reaction zone transition metal concentration ranging from any minimum transition metal concentration disclosed herein to any maximum transition metal concentration disclosed herein. In a non-limiting embodiment, the reaction zone transition metal concentration can range from $1 \times 10^{-6}$ equivalents/liter to 1 equivalent/liter, from $1 \times 10^{-5}$ equivalents/liter to 0.5 equivalents/liter, or from $5 \times 10^{-4}$ equivalents/liter to 0.1 equivalents/liter. Other transition metal concentration ranges that can be utilized are readily apparent to those of ordinary skill in the art with the aid of this disclosure. When a specific transition metal is used for the heterocyclic 2-[(phosphinyl)aminyl]imine transition metal compound complex (e.g., chromium, Cr), the reaction zone transition metal concentrations (minimum, maximum, or intermediate range) can be provided in terms of the specific transition metal of the heterocyclic 2-[(phosphinyl)aminyl]imine transition metal compound complex (e.g., a reaction zone Cr concentration).

In a non-limiting embodiment where the transition metal of the heterocyclic 2-[(phosphinyl)aminyl]imine transition metal compound complex comprises chromium, the oligomer product can be formed (or the reaction zone can operate) at a minimum reaction zone chromium concentration of the heterocyclic 2-[(phosphinyl)aminyl]imine chromium compound complex (i.e., minimum chromium concentration) of $1 \times 10^{-6}$ equivalents/liter, $1 \times 10^{-5}$ equivalents/liter, or $5 \times 10^{-4}$ equivalents/liter; additionally or alternatively, at a maximum reaction zone chromium concentration of the heterocyclic 2-[(phosphinyl)aminyl]imine chromium compound complex (i.e., maximum chromium concentration) of 1 equivalent/liter, 0.5 equivalents/liter, or 0.1 equivalents/liter. In an embodiment, the oligomer product can be formed (or the reaction zone can operate) at a reaction zone chromium concentration ranging from any minimum chromium concentration disclosed herein to any maximum chromium concentration disclosed herein. In a non-limiting embodiment, the reaction zone chromium concentration can range from $1 \times 10^{-6}$ equivalents/liter to 1 equivalent/liter, from $1 \times 10^{-5}$ equivalents/liter to 0.5 equivalents/liter, or from $5 \times 10^{-4}$ equivalents/liter to 0.1 equivalents/liter. Other reaction zone chromium concentration ranges that can be utilized are readily apparent to those of ordinary skill in the art with the aid of this disclosure.

In an embodiment, the oligomer product can be formed (or the reaction zone can operate) at a minimum pressure of 5 psi (34.5 kPa), 50 psi (345 kPa), 100 psi (689 kPa), 150 psi (1.03 MPa), 250 psi (1.72 MPa), 500 psi (3.5 MPa), or 600 psi (4.1 MPa); additionally or alternatively, at a maximum pressure of 2,500 psi (17.2 MPa), 2,000 psi (13.8 MPa), 1,500 psi (10.3 MPa), 1250 psi (8.62 MPa), or 1000 psi (6.89 MPa). In an embodiment, the oligomer product can be formed (or the reaction zone can operate) at a pressure ranging from any minimum pressure disclosed herein to any maximum pressure disclosed herein. In some non-limiting embodiments, the oligomer product can be formed (or the reaction zone can operate) at a pressure from 5 psi (34.5 kPa) to 2,500 psi (17.2 MPa), from 5 psi (34.5 kPa) to 2,000 psi (13.8 MPa), from 50 psi (345 kPa) to 2,000 psi (13.8 MPa), from 100 psi (689 kPa) to 2,000 psi (13.8 MPa), from 100 psi (689 kPa) to 1,500 psi (10.3 MPa), from 150 psi (3.5 MPa) to 1500 psi (10.3 MPa), from 250 psi (1.03 MPa) to 1250 psi (8.62 MPa), from 500 psi (1.72 MPa) to 1250 psig (6.89 MPa), or from 600 psi (4.1 MPa) to 1000 psi (9.65 MPa). Other pressure ranges that can be utilized are readily apparent to those of ordinary skill in the art with the aid of this disclosure.

In an embodiment, the oligomer product can be formed (or the reaction zone can operate) at a minimum ethylene partial pressure of 5 psi (34.5 kPa), 50 psi (345 kPa), 100 psi (689 kPa), 150 psi (1.03 MPa), 250 psi (1.72 MPa), or 500 psi (3.5 MPa); additionally or alternatively, at a maximum ethylene partial pressure of 2,500 psi (17.2 MPa), 2,000 psi (13.8 MPa), 1,500 psi (10.3 MPa), 1250 psi (8.62 MPa), or 1000 psi (6.89 MPa). In an embodiment, the oligomer product can be formed (or the reaction zone can operate) at an ethylene partial pressure ranging from any minimum ethylene partial pressure disclosed herein to any maximum ethylene partial pressure disclosed herein. In some non-limiting embodiments, the oligomer product can be formed (or the reaction zone can operate) at an ethylene partial pressure from 5 psi (34.5 kPa) to 2,500 psi (17.2 MPa), from 5 psi (34.5 kPa) to 2,000 psi (13.8 MPa), from 50 psi (345 kPa) to 2,000 psi (13.8 MPa), from 100 psi (689 kPa) to 2,000 psi (13.8 MPa), from 100 psi (689 kPa) to 1,500 psi (10.3 MPa), from 150 psi (1.03 MPa) to 1250 psi (8.62 MPa), from 250 psi (1.72 MPa) to 1000 psi (6.89 MPa), or from 500 psi (3.5 MPa) to 1000 psi (6.89 MPa). Other ethylene partial pressure ranges are readily apparent to those of ordinary skill in the art with the aid of this disclosure.

In an embodiment, the oligomer product can be formed (or the reaction zone can operate) at a minimum ethylene concentration of 4 mass %, 10 mass %, 25 mass %, 35 mass %, or 40 mass % based upon the total mass in the reaction zone; additionally or alternatively, at a maximum ethylene concentration of 70 mass %, 65 mass %, 60 mass %, 55 mass %, 50 mass %, or 48 mass % based upon the total mass in the reaction zone. In an embodiment, the oligomer product can be formed (or the reaction zone can operate) at an ethylene concentration ranging from any minimum ethylene concentration disclosed herein to any maximum ethylene concentration disclosed herein. In some non-limiting embodiments, the oligomer product can be formed (or the reaction zone can operate) at an ethylene concentration of 4 mass % to 70 mass %, 4 mass % to 65 mass %, from 10 mass % to 60 mass %, from 25 mass % to 60 mass %, from 25 mass % to 55 mass %, from 35 mass % to 50 mass %, or from 40 mass % to 48 mass % based upon the total mass in the reaction zone. Other ethylene concentration ranges that can be utilized are readily apparent to those of ordinary skill in the art with the aid of this disclosure.

In an embodiment, the oligomer product can be formed (or the reaction zone can operate) at a minimum ethylene:transition metal molar ratio of 100,000:1, 280,000:1, 460,000:1, or 750,000:1; additionally or alternatively, at a maximum ethylene:transition metal molar ratio of 9,500,000:1, 4,600,000:1, 2,800,000:1, or 1,900,000:1. In an embodiment, the oligomer product can be formed (or the reaction zone can operate) at an ethylene:transition metal molar ratio ranging from any minimum ethylene:transition metal molar ratio disclosed herein to any maximum ethylene:transition metal molar ratio disclosed herein. In some non-limiting embodiments, the oligomer product can be formed (or the reaction zone can operate) at an ethylene:transition metal molar ratio of from 100,000:1 to 9,500,000:1, 280,000:1 to 4,600,000:1, 460,000:1 to 2,800,000:1, or 750,000:1 to 1,900,000:1. Other ethylene:transition metal molar ratio ranges that can be utilized are readily apparent to those of ordinary skill in the art with the aid of this disclosure. When a specific transition metal is used for the heterocyclic 2-[(phosphinyl)aminyl]imine transition metal compound complex, the ethylene:transition metal molar ratios (minimum, maximum, or intermediate range) can be provided in terms of the specific transition metal of the heterocyclic 2-[(phosphinyl)aminyl]imine transition metal compound complex; e.g., when the transition metal of the heterocyclic 2-[(phosphinyl)aminyl]imine transition metal compound complex is chromium the ethylene:transition metal molar ratios (minimum, maximum, or intermediate range) can be stated as ethylene:chromium molar ratios.

In a non-limiting embodiment where the transition metal of the heterocyclic 2-[(phosphinyl)aminyl]imine transition metal compound complex is chromium, the oligomer product can be formed (or the reaction zone can operate) at a minimum ethylene:chromium mass ratio of 50,000:1, 150,000:1, 250,000:1, or 400,000:1; additionally or alternatively, at a maximum ethylene:chromium mass ratio of 5,000,000:1, 2,500,000:1, 1,500,000:1, or 1,000,000:1. In an embodiment, the oligomer product can be formed (or the reaction zone can operate) at an ethylene:chromium mass ratio ranging from any minimum ethylene:chromium mass ratio disclosed herein to any maximum ethylene:chromium mass ratio disclosed herein. In some non-limiting embodiments, the oligomer product can be formed (or the reaction zone can operate) at an ethylene:chromium mass ratio of from 50,000:1 to 5,000,000:1, 150,000:1 to 2,500,000:1, 250,000:1 to 1,500,000:1, or 400,000:1 to 1,000,000:1. Other ethylene:chromium mass ratio ranges that can be utilized are readily apparent to those of ordinary skill in the art with the aid of this disclosure.

In an embodiment wherein hydrogen is utilized, the oligomer product can be formed (or the reaction zone can operate) at a minimum hydrogen partial pressure of 1 psi (6.9 kPa), 2 psi (14 kPa), 5 psi (34 kPa), 10 psi (69 kPa), or 15 psi (103 kPa); alternatively or additionally, at a maximum hydrogen partial pressure of 200 psi (1.4 MPa), 150 psi (1.03 MPa), 100 psi (689 kPa), 75 psi (517 kPa), or 50 psi (345 kPa). In an embodiment, the oligomer product can be formed (or the reaction zone can operate) at a hydrogen partial pressure ranging from any minimum hydrogen partial pressure disclosed herein to any maximum hydrogen partial pressure disclosed herein. In some non-limiting embodiments wherein hydrogen is utilized, the oligomer product can be formed (or the reaction zone can operate) at a hydrogen partial pressure from 1 psi (6.9 kPa) to 200 psi (1.4 MPa), from 2 psi (14 kPa) to 150 psi (1.03 MPa), from 5 psi (34 kPa) to 100 psi (689 kPa), from 10 psi (69 kPa) to 75 psi (517 kPa), or from 15 psi (103 kPa) to 50 psi (345 kPa). Other hydrogen partial pressure ranges that can be utilized are readily apparent to those of ordinary skill in the art with the aid of this disclosure.

In an embodiment wherein hydrogen is utilized, the oligomer product can be formed (or the reaction zone can operate) at a minimum hydrogen to ethylene mass ratio of (0.05 g hydrogen)/(kg ethylene), (0.1 g hydrogen)/(kg ethylene), (0.25 g hydrogen)/(kg ethylene), (0.4 g hydrogen)/(kg ethylene), or (0.5 g hydrogen)/(kg ethylene); additionally or alternatively, at a maximum hydrogen to ethylene mass ratio of (5 g hydrogen)/(kg ethylene), (3 g hydrogen)/(kg ethylene), (2.5 g hydrogen)/(kg ethylene), (2 g hydrogen)/(kg ethylene), or (1.5 g hydrogen)/(kg ethylene). In an embodiment, the oligomer product can be formed (or the reaction zone can operate) at a hydrogen to ethylene mass ratio ranging from any minimum hydrogen to ethylene mass ratio disclosed herein to any maximum hydrogen to ethylene mass ratio disclosed herein. In some non-limiting embodiments, the oligomer product can be formed (or the reaction zone can operate) at a hydrogen to ethylene mass ratio from (0.05 g hydrogen)/(kg ethylene) to (5 g hydrogen)/(kg ethylene), from (0.1 g hydrogen)/(kg ethylene) to (5 g hydrogen)/(kg ethylene), from (0.25 g hydrogen)/(kg ethylene) to (4 g hydrogen)/(kg ethylene), from (0.25 g hydrogen)/(kg ethylene) to (3 g hydrogen)/(kg ethylene), from (0.4 g hydrogen)/(kg ethylene) to (2.5 g hydrogen)/(kg ethylene), from (0.4 g hydrogen)/(kg ethylene) to (2 g hydrogen)/(kg ethylene), from (0.5 g hydrogen)/(kg ethylene) to (2 g hydrogen)/(kg ethylene) or from (0.5 g hydrogen)/(kg ethylene) to (1.5 g hydrogen)/(kg ethylene). Other hydrogen to ethylene mass ratio ranges that can be utilized are readily apparent to those of ordinary skill in the art with the aid of this disclosure In an embodiment, the oligomer product can be formed (or the reaction zone can operate) at a minimum hydrogen:transition metal molar ratio of 26:1, 1,300:1, 2,600:1, or 5,200:1; additionally or alternatively, at a maximum hydrogen:transition metal molar ratio of 2,600,000:1, 1,300,000:1, 260,000:1, or 78,000:1. In an embodiment, the oligomer product can be formed (or the reaction zone can operate) at a hydrogen:transition metal molar ratio ranging from any minimum hydrogen:transition metal molar ratio disclosed herein to any maximum hydrogen:transition metal molar ratio disclosed herein. In some non-limiting embodiments, the oligomer product can be formed (or the reaction zone can operate) at a hydrogen:transition metal molar ratio from 26:1 to 2,600,000:1, 1,300:1 to 1,300,000:1, 2,600:1 to 260,000:1, or 5,200:1 to 78,000:1. Other hydrogen:transition metal molar ratio ranges that can be utilized are readily apparent to those of ordinary skill in the art with the aid of this disclosure. When a specific transition metal is used for the heterocyclic 2-[(phosphinyl)aminyl]imine transition metal compound complex, the hydrogen:transition metal molar ratios (minimum, maximum, or intermediate range) can be provided in terms of the specific transition metal of the heterocyclic 2-[(phosphinyl)aminyl]imine transition metal compound complex; e.g., when the transition metal of the heterocyclic 2-[(phosphinyl)aminyl]imine transition metal compound complex is chromium the hydrogen:transition metal molar ratio (minimum, maximum, or intermediate range) can be stated as hydrogen:chromium molar ratios.

In a non-limiting embodiment where the transition metal of the heterocyclic 2-[(phosphinyl)aminyl]imine transition metal compound complex is chromium, the oligomer product can be formed (or the reaction zone can operate) at a minimum hydrogen:chromium mass ratio of 1:1, 50:1, 100:1, or 200:1; additionally or alternatively, at a maximum hydrogen:chromium mass ratio of 100,000:1, 50,000:1, 10,000:1, or 3,000:1. In an embodiment, the oligomer product can be formed (or the reaction zone can operate) at a hydrogen:chromium mass ratio ranging from any minimum hydrogen:chromium mass ratio disclosed herein to any maximum hydrogen:chromium mass ratio disclosed herein. In some non-limiting embodiments, the oligomer product can be formed (or the reaction zone can operate) at a hydrogen:chromium mass ratio from 1:1 to 100,000:1, 50:1 to 50,000:1, 100:1 to 10,000:1, or 200:1 to 3,000:1. Other hydrogen:chromium mass ratio ranges that can be utilized are readily apparent to those of ordinary skill in the art with the aid of this disclosure.

In an embodiment, the oligomer product can be formed (or the reaction zone can operate) at a minimum temperature of 0° C., 25° C., 40° C., or 50° C. In some embodiments, the oligomer product can be formed (or the reaction zone can operate) at a maximum temperature of 200° C., 150° C., 100° C., or 90° C. In an embodiment, the oligomer product can be formed (or the reaction zone can operate) at a temperature ranging from any minimum temperature disclosed herein to any maximum temperature disclosed herein. In some non-limiting embodiments, the oligomer product can be formed (or the reaction zone can operate) at a temperature from 0° C. to 200° C., from 25° C. to 150° C., from 40° C. to 100° C., from 50° C. to 100° C., or from 50° C. to 90° C. Other temperature ranges that can be utilized are readily apparent to those of ordinary skill in the art with the aid of this disclosure.

The reaction time (or residence time) can comprise any time (or average time) that can produce the desired quantity of oligomer product; alternatively, any reaction time (or average reaction time, or residence time (or average residence time) that can provide a desired catalyst system productivity; alternatively, any reaction time (or average reaction time, or residence time (or average residence time) that can provide a desired ethylene conversion. Relating to forming the oligomer product, the oligomer product can be formed over a period of time (or an average time) that can produce the desired quantity of olefin product or polymer product, provide a desired catalyst system productivity, and/or provide a desired conversion of monomer. In some embodiments, the reaction time, or residence time (or average residence time) can range from 1 minute to 5 hours; alternatively, ranges from 5 minutes to 2.5 hours; alternatively, ranges from 10 minutes to 2 hours; or alternatively, ranges from 15 minutes to 1.5 hours. In some embodiments (in continuous process embodiments), the reaction time (or residence time) can be stated as an average reaction time (or average residence time) and can range from 1 minute to 5 hours; alternatively, ranges from 5 minutes to 2.5 hours; alternatively, ranges from 10 minutes to 2 hours; or alternatively, ranges from 15 minutes to 1.5 hours.

In an embodiment, the process described herein can have an ethylene conversion of at least 30%, 35%, 40%, or 45%. In another aspect, the ethylene conversion can be a single pass conversion of at least 30%, 35%, 40%, or 45%.

In an embodiment, the processes described herein can have a catalyst system productivity of greater than 500,000 grams of oligomer per mole of transition metal, greater than 2,500,000 grams of oligomer per mole of transition metal, greater than 5,000,000 grams of oligomer per mole of transition metal, greater than 7,500,000 grams of oligomer per mole of transition metal, or greater than 10,000,000 grams of oligomer per mole of transition metal. When a specific transition metal is used for the heterocyclic 2-[(phosphinyl)aminyl]imine transition metal compound complex, the catalyst system productivity can be provided in terms of the specific transition metal of the heterocyclic 2-[(phosphinyl)aminyl]imine transition metal compound complex; e.g., when the transition metal of the heterocyclic 2-[(phosphinyl)aminyl]imine transition metal compound complex is chromium the catalyst system productivity can be stated as grams of oligomer per gram of chromium. In a non-limiting embodiment where the transition metal of the heterocyclic 2-[(phosphinyl)aminyl]imine transition metal compound complex is chromium, the processes described herein can have a catalyst system productivity of greater than 5,000 grams of oligomer per gram of chromium, greater than 10,000 grams of oligomer per gram of chromium, greater than 12,500 grams of oligomer per gram of chromium, greater than 15,000 grams of oligomer per gram of chromium, or greater than 200,000 grams of oligomer per gram of chromium. In some embodiment, the grams of oligomer can be grams ($C_6+C_8$) and the catalyst system productivity can be stated as grams ($C_6+C_8$) per gram of transition metal, or specific transition metal, or chromium.

Depending upon the catalyst system utilized, the processes described herein can be an ethylene oligomerization process, an ethylene trimerization process, an ethylene tetramerization process, or an ethylene trimerization and tetramerization process; alternatively, an ethylene oligomerization process; alternatively, an ethylene trimerization process; alternatively, an ethylene tetramerization process; or alternatively an ethylene trimerization and tetramerization process. In an ethylene trimerization embodiment, the oligomer product can comprise at least 70 wt. % hexenes (ethylene trimers), at least 75 wt. % hexenes, at least 80 wt. % hexenes, at least 85 wt. % hexenes, or at least 90 wt. % hexenes based upon the weight of the oligomer product. In some ethylene trimerization embodiments, the oligomer product can comprise from 70 wt. % to 99.8 wt. % hexenes, from 75 wt. % to 99.7 wt. % hexenes, or from 80 wt. % to 99.6 wt. % hexenes based upon the weight of the oligomer product. In an ethylene tetramerization embodiment, the oligomer product can comprise at least 70 wt. % octenes (ethylene tetramers), at least 75 wt. % octenes, at least 80 wt. % octenes, at least 85 wt. % octenes, or at least 90 wt. % octenes based upon the weight of the oligomer product. In some ethylene tetramerization embodiments, the oligomer product can comprise from 70 wt. % to 99.8 wt. % octenes, from 75 wt. % to 99.7 wt. % octenes, or from 80 wt. % to 99.6 wt. % octenes based upon the weight of the oligomer product. In an ethylene trimerization and tetramerization embodiment, the oligomer product can comprise at least 70 wt. % hexenes (ethylene trimers) and octenes (ethylene tetramers), at least 75 wt. % hexenes and octenes, at least 80 wt. % hexenes and octenes, at least 85 wt. % hexene and octenes, or at least 90 wt. % hexenes and octenes based upon the weight of the oligomer product. In some ethylene trimerization and tetramerization embodiments, the oligomer product can comprise from 70 wt. % to 99.8 wt. % hexenes and octenes, from 75 wt. % to 99.7 wt. % hexenes and octenes, or from 80 wt. % to 99.6 wt. % hexenes and octenes based upon the weight of the oligomer product.

In ethylene oligomerization, ethylene trimerization, or ethylene trimerization and tetramerization embodiments, the ethylene trimer can comprise at least 85 wt. % 1-hexene; alternatively, at least 87.5 wt. % 1-hexene; alternatively, at least 90 wt. % 1-hexene; alternatively, at least 92.5 wt. % 1-hexene; alternatively, at least 95 wt. % 1-hexene; alternatively, at least 97 wt. % 1-hexene; or alternatively, at least 98 wt. % 1-hexene by weight of the ethylene trimer, or from 85 wt. % to 99.9 wt. % 1-hexene; alternatively, from 87.5 wt. % to 99.9 wt. % 1-hexene; alternatively, from 90 wt. % to 99.9 wt. % 1-hexene; alternatively, from 92.5 wt. % to 99.9 wt. % 1-hexene; alternatively, from 95 wt. % to 99.9 wt. % 1-hexene; alternatively, from 97 wt. % to 99.9 wt. % 1-hexene; or alternatively, from 98 wt. % to 99.9 wt. % 1-hexene by weight of the ethylene trimer.

In ethylene oligomerization, ethylene tetramerization, or ethylene trimerization and tetramerization embodiments, the ethylene tetramer can comprise at least 85 wt. % 1-octene; alternatively, at least 87.5 wt. % 1-octene; alternatively, at least 90 wt. % 1-octene; alternatively, at least 92.5 wt. % 1-octene; alternatively, at least 95 wt. % 1-octene; alternatively, at least 97 wt. % 1-octene; or alternatively at least 98 wt. % 1-octene by weight of the ethylene tetramer or from 85 wt. % to 99.9 wt. % 1-octene; alternatively, from 87.5 wt. % to 99.9 wt. % 1-octene; alternatively, from 90 wt. % to 99.9 wt. % 1-octene; alternatively, from 92.5 wt. % to 99.9 wt. % 1-octene; alternatively, from 95 wt. % to 99.9 wt. % 1-octene; alternatively, from 97 wt. % to 99.9 wt. % 1-octene; or alternatively, from 98 wt. % to 99.9 wt. % 1-octene by weight of the ethylene tetramer.

Processes described herein can use organic liquid medium and/or an organic reaction medium. Generally, the organic liquid medium and/or organic reaction medium can act as a solvent and/or a diluent in the processes described herein. In an embodiment, the organic liquid medium and/or organic reaction medium can be a hydrocarbon, a halogenated hydrocarbon, or a combination thereof. Hydrocarbons and halogenated hydrocarbons which can be used as the organic reaction medium can include, for example, aliphatic hydrocarbons, aromatic hydrocarbons, petroleum distillates, halogenated aliphatic hydrocarbons, halogenated aromatic hydrocarbons, or combinations thereof. Aliphatic hydrocarbons which can be utilized as the organic liquid medium and/or organic reaction medium include $C_3$ to $C_{20}$ aliphatic hydrocarbons, or $C_4$ to $C_{15}$ aliphatic hydrocarbons, or $C_5$ to $C_{10}$ aliphatic hydrocarbons, for example. The aliphatic hydrocarbons which can be used as the organic liquid medium and/or organic reaction medium can be heterocyclic or acyclic and/or can be linear or branched, unless otherwise specified. Non-limiting examples of suitable acyclic aliphatic hydrocarbon organic liquid medium and/or organic reaction mediums that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or a mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), or combinations thereof. Non-limiting examples of suitable cyclic aliphatic hydrocarbons which can be utilized as the organic liquid medium and/or organic reaction medium include cyclohexane, and methyl cyclohexane. Aromatic hydrocarbons which can be utilized as the organic reaction medium include $C_6$ to $C_{10}$ aromatic hydrocarbons. Non-limiting examples of suitable aromatic hydrocarbons that can be utilized singly or in any combination as the organic liquid medium and/or organic reaction medium include benzene, toluene, xylene (including ortho-xylene, meta-xylene, para-xylene, or mixtures thereof), ethylbenzene, or combinations thereof. Halogenated aliphatic hydrocarbons which can be utilized as the organic liquid medium and/or organic reaction medium include $C_1$ to $C_{15}$ halogenated aliphatic hydrocarbons, $C_1$ to $C_{10}$ halogenated aliphatic hydrocarbons, or $C_1$ to $C_5$ halogenated aliphatic hydrocarbons. The halogenated aliphatic hydrocarbons which can be utilized as the organic liquid medium and/or organic reaction medium can be cyclic or acyclic and/or can be linear or branched, unless otherwise specified. Non-limiting examples of suitable halogenated aliphatic hydrocarbons which can be utilized as the organic liquid medium and/or organic reaction medium include methylene chloride, chloroform, carbon tetrachloride, dichloroethane, trichloroethane, and combinations thereof. Halogenated aromatic hydrocarbons which can be utilized as the organic liquid medium and/or organic reaction medium include $C_6$ to $C_{20}$ halogenated aromatic hydrocarbons, or $C_6$ to $C_{10}$ halogenated aromatic hydrocarbons. Non-limiting examples of suitable halogenated aromatic hydrocarbons which can be utilized as the organic liquid medium and/or organic reaction medium include chlorobenzene, dichlorobenzene, or combinations thereof.

The choice of the organic liquid medium and/or organic reaction medium can be made on the basis of convenience in processing. For example, isobutane can be chosen to be compatible with the organic liquid medium and/or organic reaction medium used in processes using the product(s) of the process described herein (e.g., using the product for the formation of polymer in a subsequent processing step). In some embodiments, the organic liquid medium and/or organic reaction medium can be chosen to be easily separable from one or more of the oligomers in the oligomer product. In some embodiments, an oligomer of the oligomer product can be utilized as the organic liquid medium and/or organic reaction medium. For example, when 1-hexene is the oligomer of an ethylene trimerization process, 1-hexene can be chosen as the organic liquid medium and/or organic reaction medium to decrease the need for separation.

Various aspects and embodiments described herein can refer to a substituted group or compound. In an embodiment, each substituent of any aspect or embodiment calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In an embodiment, each hydrocarbyl substituent can be a $C_1$ to $C_{10}$ hydrocarbyl group; or alternatively, a $C_1$ to $C_5$ hydrocarbyl group. In an embodiment, each hydrocarboxy group can be a $C_1$ to $C_{10}$ hydrocarboxy group; or alternatively, a $C_1$ to $C_5$ hydrocarboxy group.

In an embodiment, any halide substituent of any aspect or embodiment calling for a substituent can be a fluoride, chloride, bromide, or iodide; alternatively, a fluoride or chloride. In some embodiments, any halide substituent of any aspect or embodiment calling for a substituent can be a fluoride; alternatively, a chloride; alternatively, a bromide; or alternatively, an iodide.

In an embodiment, any hydrocarbyl substituent of any aspect or embodiment calling for a substituent can be an alkyl group, an aryl group, or an aralkyl group; alternatively, an alkyl group; alternatively, an aryl group; or alternatively, an aralkyl group. In an embodiment, any alkyl substituent of any aspect or embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of any aspect or embodiment calling for a substituent can be a phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl substituent of any aspect or embodiment calling for a substituent can be benzyl group or an ethylphenyl group (2-phenyleth-1-yl or 1-phenyleth-1-yl); alternatively, a benzyl group; alternatively, an ethylphenyl group; alternatively, a 2-phenyleth-1-yl group; or alternatively, a 1-phenyleth-1-yl group.

In an embodiment, any hydrocarboxy substituent of any aspect or embodiment calling for a substituent can be an alkoxy group, an aryloxy group, or an aralkoxy group; alternatively, an alkoxy group; alternatively, an aryloxy group, or an aralkoxy group. In an embodiment, any alkoxy substituent of any aspect or embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy substituent of any aspect or embodiment calling for a substituent can be phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an embodiment, any aralkoxy substituent of any aspect or embodiment calling for a substituent can be benzoxy group.

ADDITIONAL DISCLOSURE

Accordingly, the scope of protection is not limited by the description set out above but is only limited by the claims which follow, that scope including all equivalents of the subject matter of the claims. Each and every claim is incorporated into the specification as an aspect of the subject matter of the present disclosure. Thus, the claims are a further description and are an addition to the detailed description of the present disclosure. The disclosures of all patents, patent applications, and publications cited herein are hereby incorporated by reference in their entirety.

Having described the various compounds, complexes, and processes, aspects and embodiments of those compounds, complexes, and/or processes can include, but are not limited to the following additional embodiments.

Embodiment 1

A Catalyst System Comprising i) a Heterocyclic 2-[(phosphinyl)aminyl]imine Transition Metal Compound Complex Having Structure HCPAITMC 1

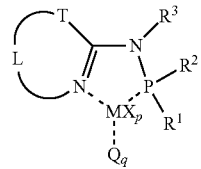

Structure HCPAITMC 1 wherein T is oxygen or sulfur, $R^1$ and $R^2$ are each independently a $C_1$ to $C_{20}$ organyl group consisting essentially of inert functional groups, $R^3$ is hydrogen or a $C_1$ to $C_{20}$ organyl group, L is a $C_1$ to $C_{20}$ organylene group consisting essentially of inert functional groups, $MX_p$ represents a transition metal compound where M is a transition metal, X is a monoanion, and p is an integer from 1 to 6, Q is a neutral ligand, and q ranges from 0 to 6, and ii) an organoaluminum compound.

Embodiment 2. The catalyst system of embodiment 1, wherein the heterocyclic 2-[(phosphinyl)aminyl]imine transition metal compound complex has Structure HCPAITMC 2, Structure HCPAITMC 3, Structure HCPAITMC 4, Structure HCPAITMC 5, or Structure HCPAITMC 6

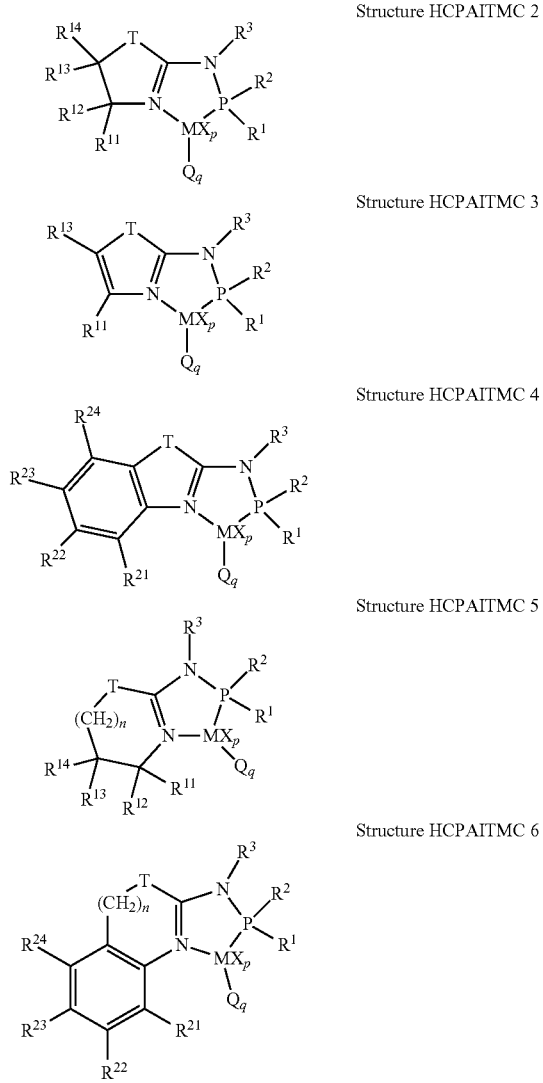

wherein n is 1 or 2, T is oxygen or sulfur; $R^1$ and $R^2$ are each independently a $C_1$ to $C_{20}$ organyl group consisting essentially of inert functional groups; $R^3$ is hydrogen or a $C_1$ to $C_{20}$ organyl group; $R^{11}$ is hydrogen or a $C_1$ to $C_{20}$ organyl group consisting essentially of inert functional groups; $R^{12}$, $R^{13}$, $R^{14}$, $R^{21}$, $R^{22}$, $R^{23}$, and $R^{24}$ are each independently hydrogen or a $C_1$ to $C_{20}$ organyl group consisting essentially of inert functional groups; optionally $R^{11}$ or $R^{12}$ and $R^{13}$ or $R^{14}$ are joined to form a ring or ring system; $MX_p$ represents a transition metal compound where M is a transition metal, X is a monoanion, and p is an integer from 2 to 6; Q is a neutral ligand; and q ranges from 0 to 6.

Embodiment 3. The catalyst system of embodiment 2, wherein $R^{11}$ is hydrogen or a $C_1$ to $C_{10}$ alkyl group and $R^{12}$, $R^{13}$, and $R^{14}$ are hydrogen; $R^{21}$ is hydrogen or a $C_1$ to $C_{10}$ alkyl group; and $R^{22}$, $R^{23}$, and $R^{24}$ are hydrogen.

Embodiment 4. The catalyst system of any one of embodiments 1 to 3, wherein $R^3$ is hydrogen.

Embodiment 5. A process comprising: contacting i) ethylene, ii) a catalyst system comprising (a) a heterocyclic 2-[(phosphinyl)aminyl]imine transition metal compound complex having Structure HCPAITMC 1:

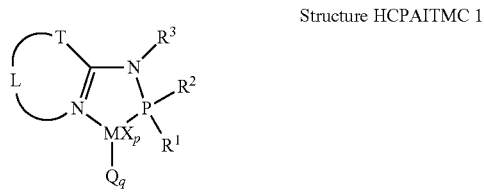

wherein T is oxygen or sulfur, $R^1$ and $R^2$ are each independently a $C_1$ to $C_{20}$ organyl group consisting essentially of inert functional groups, $R^3$ is hydrogen or a $C_1$ to $C_{20}$ organyl group, L is a $C_1$ to $C_{20}$ organylene group consisting essentially of inert functional groups, $MX_p$ represents a transition metal compound where M is a transition metal, X is a monoanion, and p is an integer from 2 to 6, Q is a neutral ligand; and q ranges from 0 to 6, and (b) an organoaluminum compound, and iii) optionally hydrogen to form an oligomer product.

Embodiment 6. The process of embodiment 5, wherein the heterocyclic 2-[(phosphinyl)aminyl]imine transition metal compound complex has Structure HCPAITMC 2, Structure HCPAITMC 3, Structure HCPAITMC 4, Structure HCPAITMC 5, or Structure HCPAITMC 6:

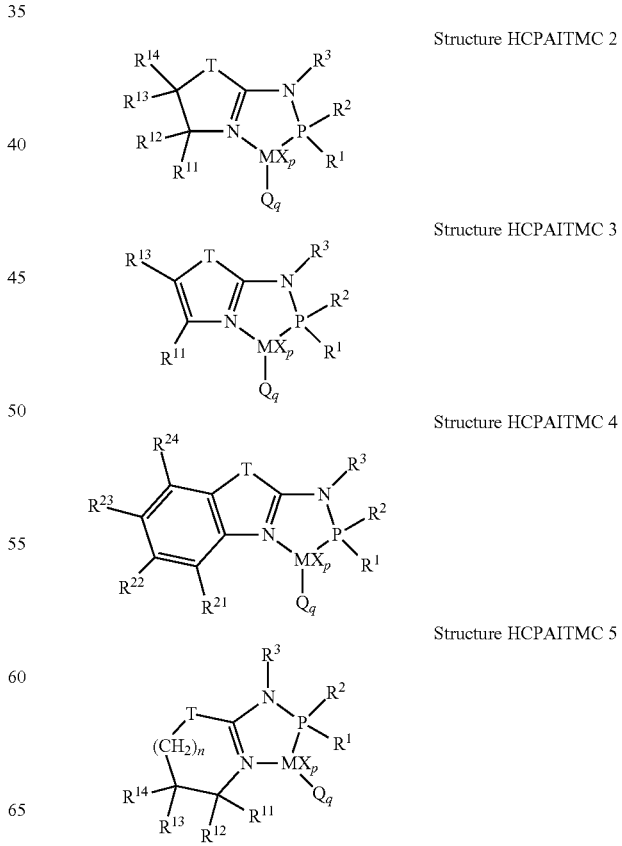

-continued

Structure HCPAITMC 6

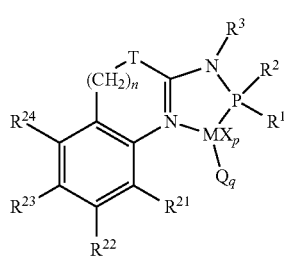

wherein n is 1 or 2, T is oxygen or sulfur, $R^1$ and $R^2$ are each independently a $C_1$ to $C_{20}$ organyl group consisting essentially of inert functional groups, $R^3$ is hydrogen or a $C_1$ to $C_{20}$ organyl group, $R^{11}$ is hydrogen or a $C_1$ to $C_{20}$ organyl group consisting essentially of inert functional groups, $R^{12}$, $R^{13}$, $R^{14}$, $R^{21}$, $R^{22}$, $R^{23}$, and $R^{24}$ are each independently hydrogen or a $C_1$ to $C_{20}$ organyl group consisting essentially of inert functional groups, optionally $R^{11}$ or $R^{12}$ and $R^{13}$ or $R^{14}$ are joined to form a ring or ring system, $MX_p$ represents a transition metal compound where M is a transition metal, X is a monoanion, and p is an integer from 1 to 6, Q is a neutral ligand, and q ranges from 0 to 6.

Embodiment 7. The process of any one of embodiments 5 to 6, wherein the process further comprises contacting the heterocyclic 2-[(phosphinyl)aminyl]imine transition metal compound complex and the organoaluminum compound to form a catalyst system mixture, and aging the catalyst system mixture in a substantial absence of ethylene to form an aged catalyst system mixture.

Embodiment 8. The process of embodiment 7, wherein the catalyst system is aged in the substantial absence of ethylene for from 5 minutes to 6 hours.

Embodiment 9. The process of any one of embodiments 5 to 8, wherein the oligomer product is formed in a reaction zone.

Embodiment 10. The process of embodiment 9, wherein the oligomer product is formed at (or the reaction zone has) any temperature disclosed herein, e.g., at least 0° C., 25° C., 40° C., or 50° C., in a range of 0° C. to 200° C., 25° C. to 150° C., 40° C. to 100° C., 50° C. to 100° C., or 50° C. to 90° C., etc.

Embodiment 11. The process of any one of embodiments 9 or 10, wherein the oligomer product is formed at (or the reaction zone has) any ethylene partial pressure disclosed herein, e.g., at least 5 psi (34.5 kPa), 50 psi (345 kPa); 250 psi (1.72 MPa), or 500 psi (3.5 MPa), in the range of 5 psi (34.5 kPa) to 2,500 psi (17.2 MPa), from 5 psi (34.5 kPa) to 2,000 psi (13.8 MPa), from 100 psi (689 kPa) to 2,000 psi (13.8 MPa), from 150 psi (1.03 MPa) to 1250 psi (8.62 MPa), from 250 psi (1.72 MPa) to 1000 psi (6.89 MPa), or from 500 psi (3.5 MPa) to 1000 psi (6.89 MPa), etc.

Embodiment 12. The process of any one of embodiments 9 to 11, wherein the oligomer product is formed at (or the reaction zone has) any minimum ethylene:transition metal mass ratio disclosed herein, e.g., 50,000:1, 150,000:1, 250,000:1, or 400,000:1, in the range of 50,000:1 to 5,000,000:1, 150,000:1 to 2,500,000:1, 250,000:1 to 1,500,000:1, or 400,000:1 to 1,000,000:1, etc.

Embodiment 13. The process of any one of embodiments 9 to 12, wherein the oligomer product is formed at (or the reaction zone has) any aluminum of the organoaluminum compound to transition metal of the heterocyclic 2-[(phosphinyl)aminyl]imine transition metal compound complex molar ratio disclosed herein, e.g., at least 10:1, 50:1, 75:1 or 100:1, in the range of 10:1 to 5,000:1, from 50:1 to 3,000:1, from 75:1 to 2,000:1, from 100:1 to 1,500:1, of from 100:1 to 1,000:1, etc.

Embodiment 14. The process of any one of embodiments 9 to 13, wherein the transition metal is chromium and the oligomer product is formed at (or the reaction zone has) any aluminum of the organoaluminum compound to chromium of the heterocyclic 2-[(phosphinyl)aminyl]imine transition metal compound complex molar ratio disclosed herein, e.g., at least 10:1, 50:1, 75:1, or 100:1, in the range of 10:1 to 5,000:1, from 50:1 to 3,000:1, from 75:1 to 2,000:1, from 100:1 to 1,500:1, of from 100:1 to 1,000:1, etc.

Embodiment 15. The process of any one of embodiments 9 to 14, wherein the oligomer product is formed in the presence of an organic reaction medium.

Embodiment 16. The process of any one of embodiments 9 to 15, wherein the transition metal is chromium and the oligomer product is formed at (or the reaction zone) has any chromium concentration of the heterocyclic 2-[(phosphinyl)aminyl]imine transition metal compound complex disclosed herein, e.g., at least $1 \times 10^{-6}$ Cr equivalents/liter, $1 \times 10^{-5}$ Cr equivalents/liter, or $5 \times 10^{-4}$ Cr equivalents/liter, in the range of $1 \times 10^{-6}$ Cr equivalents/liter to 1 Cr equivalents/liter, $1 \times 10^{-5}$ Cr equivalents/liter to 0.5 Cr equivalents/liter, $5 \times 10^{-4}$ Cr equivalents/liter to 0.1 Cr equivalents/liter, etc.

Embodiment 17. The process of any one of embodiments 9 to 16, wherein the oligomer product is formed at (or the reaction zone has) any ethylene concentration disclosed herein, e.g., at least 4 mass %, 10 mass %, 25 mass %, 35 mass %, or 40 mass %, in the range of 4 mass % to 70 mass %, from 4 mass % to 65 mass %, from 10 mass % to 60 mass %, from 25 mass % to 60 mass %, 25 mass % to 55 mass %, 35 mass % to 50 mass %, or 40 mass % to 48 mass %, etc. based upon the total mass in the reaction zone.

Embodiment 18. The process of any one of embodiments 9 to 17, wherein the process further comprises contacting hydrogen with the ethylene, the catalyst system, and/or an optional organic reaction medium.

Embodiment 19. The process any one of embodiments 9 to 18, wherein the oligomer product is formed at (or the reaction zone has) any hydrogen partial pressure disclosed herein, e.g., at least 1 psi (6.9 kPa), 2 psi (14 kPa), 5 psi (34 kPa), 10 psi (69 kPa), or 15 psi (103 kPa), in the range of 1 psi (6.9 kPa) to 200 psi (1.4 MPa), from 2 psi (14 kPa) to 150 psi (1.03 MPa), from 5 psi (34 kPa) to 100 psi (689 kPa), from 10 psi (69 kPa) to 75 psi (517 kPa), or from 15 psi (103 kPa) to 50 psi (345 kPa), etc.

Embodiment 20. The process of any one of embodiments 9 to 19, wherein the oligomer product is formed at (or the reaction zone has) any hydrogen to ethylene mass ratio disclosed herein, e.g., at least (0.05 g hydrogen)/(kg ethylene), (0.1 g hydrogen)/(kg ethylene), (0.25 g hydrogen)/(kg ethylene), (0.4 g hydrogen)/(kg ethylene), or (0.5 g hydrogen)/(kg ethylene), in the range of (0.05 g hydrogen)/(kg ethylene) to (5 g hydrogen)/(kg ethylene), from (0.1 g hydrogen)/(kg ethylene) to (5 g hydrogen)/(kg ethylene), (0.25 g hydrogen)/(kg ethylene) to (4 g hydrogen)/(kg ethylene), (0.4 g hydrogen)/(kg ethylene) to (3 g hydrogen)/(kg ethylene), (0.4 g hydrogen)/(kg ethylene) to (2.5 g hydrogen)/(kg ethylene), (0.4 g hydrogen)/(kg ethylene) to (2 g hydrogen)/(kg ethylene), or (0.5 g hydrogen)/(kg ethylene) to (1.5 g hydrogen)/(kg ethylene), etc.

Embodiment 21. The process of any one of embodiments 9 to 20, wherein the oligomer product is formed at (or the reaction zone has) any hydrogen:chromium mass ratio disclosed herein, e.g., at least 1:1, 50:1, 100:1, or 200:1, in the range of 1:1 to 100,000:1, 50:1 to 50,000:1, 100:1 to 10,000:1, or 200:1 to 3,000:1, etc.

Embodiment 22. The process of any one of embodiments 9 to 21, wherein the oligomer product is formed at (or the reaction zone has) (a) an ethylene partial pressure ranging from 150 psi to 2,000 psi, (b) a hydrogen partial pressure ranging from 5 psi to 400 psi, (c) a temperature ranging from 20° C. to 150° C., and (d) an aluminum of the aluminoxane to transition metal of the heterocyclic 2-[(phosphinyl)aminyl]imine transition metal compound complex molar ratio is in the range of from 10:1 to 5,000:1.

Embodiment 23. The process of any one of embodiments 5 to 22, wherein the oligomer product comprises any amount of hexenes, octenes, or any combination thereof described herein.

Embodiment 24. The process of any one of embodiments 5 to 23, wherein an ethylene trimer has any 1-hexene content disclosed herein, e.g., at least 90 wt. %, at least 92.5 wt. %, at least 95 wt. %, at least 97 wt. %, or at least 98 wt. % 1-hexene, from 85 wt. % to 99.9 wt. %, from 87.5 wt. % to 99.9 wt. %, from 90 wt. % to 99.9 wt. %, from 92.5 wt. % to 99.9 wt. %, from 95 wt. % to 99.9 wt. %, from 97 wt. % to 99.9 wt. %; or from 98 wt. % to 99.9 wt. % 1-hexene, etc.

Embodiment 25. The process of any one of embodiments 5 to 24, wherein an ethylene tetramer has any 1-octene content disclosed herein, e.g., at least 90 wt. %, at least 92.5 wt. %, at least 95 wt. %, at least 97 wt. %, or at least 98 wt. % 1-octene, from 90 wt. % to 99.9 wt. %, from 92.5 wt. % to 99.9 wt. %, from 95 wt. % to 99.9 wt. %, from 97 wt. % to 99.9 wt. %, or from 98 wt. % to 99.9 wt. % 1-octene, etc.

Embodiment 26. The subject matter of any one of embodiments 1 to 25, wherein the organoaluminum compound comprises an aluminoxane.

Embodiment 27. The subject matter of embodiment 26, wherein the aluminoxane comprises methylaluminoxane, a modified methylaluminoxane, ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, or mixtures thereof.

Embodiment 28. The subject matter of any one of embodiments 26 or 27, wherein the aluminoxane comprises a modified methylaluminoxane.

Embodiment 29. The subject matter of any one of embodiments 1 to 28, wherein each X independently is a halide, a carboxylate, or a β-diketonate.

Embodiment 30. The subject matter of any one of embodiments 1 to 29, wherein the transition metal compound comprises a chromium(III) carboxylate, a chromium (III) β-diketonate, or a chromium(III) halide.

Embodiment 31. The subject matter of any one of embodiments 1 to 30, wherein the transition metal compound is chromium (III) chloride or chromium (III) acetylacetonate.

Embodiment 32. The subject matter of any one of embodiments 1 to 31, wherein the heterocyclic 2-[(phosphinyl)aminyl]imine transition metal compound complex has Structure HCPAITMC 2, Structure HCPAITMC 3, Structure HCPAITMC 4, Structure HCPAITMC 5, or Structure HCPAITMC 6:

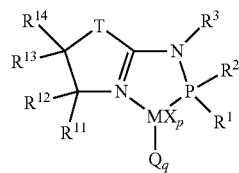

Structure HCPAITMC 2

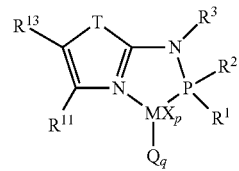

Structure HCPAITMC 3

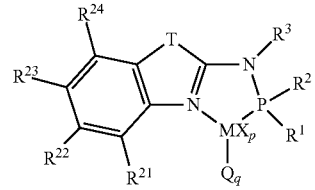

Structure HCPAITMC 4

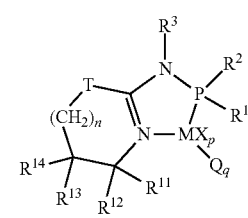

Structure HCPAITMC 5

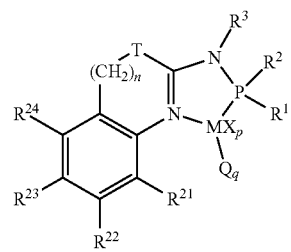

Structure HCPAITMC 6 wherein n is 1 or 2, T is oxygen or sulfur, $R^1$ and $R^2$ are each independently a $C_1$ to $C_{20}$ organyl group consisting essentially of inert functional groups, $R^3$ is hydrogen, $R^{11}$ is hydrogen of a $C_1$ to $C_{10}$ alkyl group and $R^{12}$, $R^{13}$, and $R^{14}$ are hydrogen, $R^{21}$ is hydrogen or a $C_1$ to $C_{10}$ alkyl group, and $R^{22}$, $R^{23}$, and $R^{24}$ are hydrogen, $MX_p$ is chromium(III) chloride, Q is a neutral ligand, q ranges from 0 to 6, the organoaluminum compound is an aluminoxane, and an aluminum of the aluminoxane to chromium of the heterocyclic 2-[(phosphinyl)aminyl]imine transition metal compound complex molar ratio is in the range of from 10:1 to 5,000:1.

Embodiment 33. The subject matter of any one of embodiment 1 to 32, wherein each neutral ligand independently can be any neutral ligand disclosed herein, e.g., any nitrile, ether, or amine disclosed herein, any a nitrile or ether disclosed herein, any nitrile disclosed herein, or any ether disclosed herein, etc.

Embodiment 34. The subject matter of any one of embodiments 1 to 33, wherein the heterocyclic 2-[(phosphinyl)aminyl]imine transition metal compound complex has Structure HCPAICr A, Structure HCPAICr B, or Structure HCPAICr C:

Structure HCPAlCr A

Structure HCPAlCr B

Structure HCPAlCr C

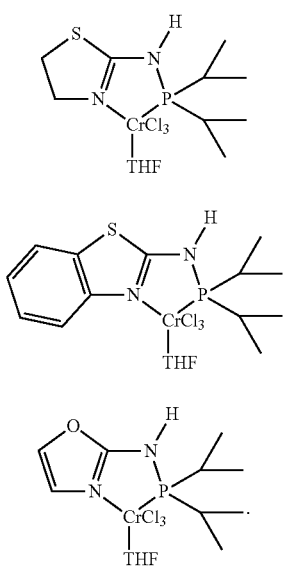

HCPAlCr C

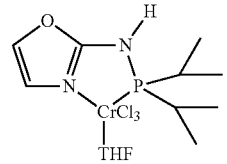

APClCr I

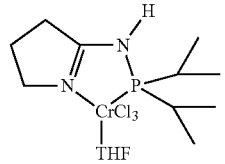

NPACr I

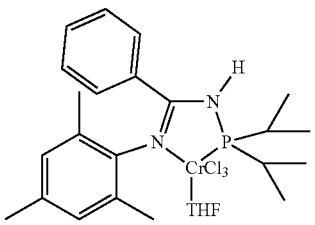

EXAMPLES

The subject matter of the present disclosure having been generally described, the following examples are given as particular aspects of the disclosure and to demonstrate the practice and advantages thereof. It is understood that the examples are given by way of illustration and are not intended to limit the specification or the claims to follow in any manner.

Heterocyclic 2-[(phosphinyl)aminyl]imine chromium(III) chloride complexes HCPAlCr A, HCPAlCr B, and HCPAlCr C were individually prepared and utilized separately as a component in an ethylene oligomerization catalyst system. The 2[(phosphinyl)aminyl] cyclic imine chromium(III) chloride complex having Structure APClCr I was prepared utilizing methods described in U.S. patent application Ser. No. 15/171,170 filed on Jun. 2, 2016, now U.S. Pat. No 10,196,328 B2, The N²-phosphinyl amidine chromium(III) chloride complex having Structure NPACr I was prepared utilizing methods described in U.S. Patent Application Publication US 2012/0309965 A1.

HCPAlCr A

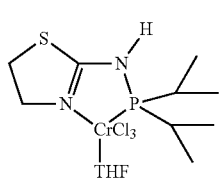

HCPAlCr B

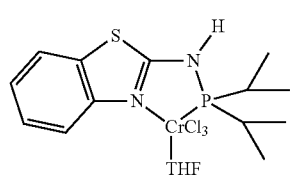

Anhydrous tetrahydrofuran, THF, was obtained from Sigma-Aldrich and stored over 13× molecular sieves until utilized. 2-amino-2-thiazoline was obtained from Acros and utilized without further treatment or purification. 2-amino benzothiazole was obtained from Sigma-Aldrich and utilized without further treatment or purification. 2-aminoxazole was obtained from Sigma-Aldrich and utilized without further treatment or purification. Chlorodiisopropylphosphine was obtained from Sigma-Aldrich and utilized without further treatment or purification. $CrCl_3(THF)_3$ was obtained from Strem and utilized without further treatment or purification. MMAO-20, 7 wt. % aluminum in heptanes, was utilized as obtained from AkzoNobel Functional Chemicals B.V. Ethylbenzene, anhydrous, was obtained from Sigma-Aldrich and stored over 13× mol sieves until utilized. Cyclohexane, anhydrous, was obtain from Sigma-Aldrich and was stored over 13× mol sieves until utilized. Ethylene, from Matheson Grade cylinder supplied by Matheson, was utilized as supplied.

Example 1

Preparation of 2-[(diisopropylphosphinyl)amino imine Heterocycles

Preparation of 2-[(diisopropylphosphinyl)amino Thiazoline

In an inert atmosphere glove box, 2-amino-2-thiazoline (2.0 g, 20 mmol) was suspended in diethyl ether with stirring. To the suspension was added n-butyllithium (20 mmol) dropwise over 15 minutes. This mixture was allowed to stir for 3 hours. To the resulting suspension was added chlorodiisopropylphosphine (2.9 g, 19 mmol) dropwise with stirring. The resulting mixture was allowed to stir overnight then filtered on a glass frit. The volatiles were removed from the filtrate in vacuo and the resulting yellow semi-solids were suspended and stirred in pentane resulting in white solids which were collected on a frit. The white solids were dried in vacuo then analyzed by GC-MS and confirmed as 2-[(diisopropylphosphinyl)amino thiazoline (1.04 g, 4.76 mmol).

Preparation of 2-[(diisopropylphosphinyl)amino Benzothiazole

In an inert atmosphere glove box, 2-amino benzothiazole (1.0 g, 6.6 mmol) was suspended in diethyl ether with stirring. To the suspension was added n-butyllithium (6.6 mmol) dropwise over 15 minutes. This mixture was allowed to stir for 2 hours. To the resulting cloudy suspension was added chlorodiisopropylphosphine (1.0 g, 6.6 mmol) dropwise with stirring. The resulting mixture was allowed to stir overnight. The following morning, peach colored solids were filtered away on a glass frit. The volatiles were slowly evaporated from the filtrate resulting in colorless crystals. The remaining yellow filtrate was removed, the colorless crystals were analyzed by GC-MS and confirmed as 2-[(diisopropylphosphinyl)amino benzothiazole (0.522 g, 1.96 mmol).

Preparation of 2-[(diisopropylphosphinyl)amino Oxazole

In an inert atmosphere glove box, 2-amino oxazole (1.0 g, 11.9 mmol) was suspended in diethyl ether with stirring. To the suspension was added n-butyllithium (11.9 mmol) dropwise over 15 minutes. This mixture was allowed to stir for 5 hours. To the resulting cloudy suspension was added chlorodiisopropylphosphine (1.8 g, 11.8 mmol) dropwise with stirring. The resulting yellow solution was allowed to stir overnight. The following morning, the resulting orange mixture was filtered on a glass frit. The volatiles were removed from the filtrate in vacuo and the resulting yellow semi-solids were suspended and stirred in a mixture of in pentane and diethyl ether. White solids were then filtered off on a frit. The yellow filtrate was dried in vacuo resulting in a yellow oil which was analyzed by GC-MS and confirmed as 2-[(diisopropylphosphinyl)amino oxazole (0.750 g, 3.75 mmol).

Example 2

Preparation of Chromium Chloride—THF Complexes

Preparation of 2-[(diisopropylphosphinyl)amino Thiazoline Chromium(III) Chloride Tetrahydrofuran Complex—HCPAlCr A In an inert atmosphere glove box, $CrCl_3(THF)_3$ (0.348 g, 0.929 mmol) was suspended in tetrahydrofuran with stirring. To the suspension was added a solution of 2-[(diisopropylphosphinyl)amino thiazoline (0.214 g, 0.980 mmol) in tetrahydrofuran dropwise with stirring. The resulting suspension was allowed to stir overnight. From the resultant blue solution, the solvent was removed in vacuo. The resulting solids were stirred in diethyl ether then filtered. The blue solids were collected, and subsequently used as HCPAlCr A.

Preparation of 2-[(diisopropylphosphinyl)amino Benzothiazole Chromium(III) Chloride Tetrahydrofuran Complex—HCPAlCr B In an inert atmosphere glove box, $CrCl_3(THF)_3$ (0.267 g, 0.713 mmol) was suspended in tetrahydrofuran with stirring. To the suspension was added 2-[(diisopropylphosphinyl) amino benzothiazole (0.200 g, 0.751 mmol) as a solid. The resulting suspension was stirred four hours. From the resultant blue solution, the solvent was removed in vacuo. The resulting solids were stirred in diethyl ether then filtered. The blue solids were collected, and subsequently used as HCPAlCr B.

Preparation of 2-[(diisopropylphosphinyl)amino Oxazole Chromium(III) Chloride Tetrahydrofuran Complex—HCPAlCr C In an inert atmosphere glove box, $CrCl_3(THF)_3$ (0.715 g, 1.91 mmol) was suspended in tetrahydrofuran with stirring. To the suspension was added 2-[(diisopropylphosphinyl) amino oxazole (0.400 g, 2.00 mmol) as a solid. The resulting suspension was allowed to stir overnight. From the resultant blue solution, the solvent was removed in vacuo. The resulting solids were stirred in diethyl ether then filtered. The blue solids were collected, and subsequently used as HCPAlCr C.

Example 3

General Ethylene Oligomerization Procedure—Runs 1-6

Ethylene oligomerizations were performed using heterocyclic 2-[(phosphinyl)aminyl]imine chromium(III) chloride complexes HCPAlCr A, HCPAlCr B, and HCPAlCr C, 2-[(phosphinyl)aminyl]cyclic imine chromium(III) chloride complex APClCr I, and $N^2$-phosphinyl amidine chromium (III) chloride complex NPACr I using the following procedure and the amounts and conditions indicated in Table 2.

In a dry box, a 20 mL glass vial was charged with the desired complex, the desired amount of catalyst system solvent, and MMAO-20 (7 wt. % Al solution in heptanes) or MMAO-3 (7 wt. % Al solution in heptanes) to provide the desired Al:Cr molar ratio. This solution was then aged for the desired time in the absence of ethylene to provide an aged catalyst system mixture. The aged catalyst system mixture was then added to 0.5 L glass charger containing 200 mL of the oligomerization solvent, cyclohexane.

The glass charger was removed from the dry box and the contents charged into an evacuated 0.5 L stainless steel reactor having an internal temperature of 60° C. Hydrogen was charged to the stainless-steel reactor to the desired pressure. Ethylene was then charged to the stainless-steel reactor to the desired pressure. The reaction was allowed to proceed at the conditions indicated in Table 2 with ethylene being fed on demand to maintain the desired oligomerization pressure.

At reaction completion, water cooling was applied to the 0.5 L stainless steel reactor using the internal cooling coils. When the stainless-steel reactor contents reached 35° C., the unreacted ethylene and hydrogen gas were vented from the stainless-steel reactor. A 2 mL sample of the liquid product was collected, filtered, and analyzed by GC-FID. The stainless-steel reactor solids were collected by filtering the liquid solution and cleaning the reactor walls and internal cooling coils. Table 2 provides the analysis of the oligomer product of the ethylene oligomerization and the calculated productivities and activity of the catalyst systems tested in ethylene oligomerization runs 1-6.

TABLE 2

| Ethylene Oligomerization Run # | 1 | 2 | 3 | 4 | 5 | 6 |
|---|---|---|---|---|---|---|
| Catalyst System | | | | | | |
| Complex | HCPAlCr A | HCPAlCr B | HCPAlCr C | HCPAlCr C | APClCr I | NPACr I |
| Mass Complex (mg) | 3.5 | 3.5 | 2.5 | 2.5 | 2.5 | 3.5 |
| mmol complex | 0.0078 | 0.0070 | 0.0058 | 0.0058 | 0.0058 | 0.0060 |
| mg Cr | 0.4056 | 0.3663 | 0.3018 | 0.3018 | 0.3018 | 0.3112 |
| Catalyst System Solvent* | EB | EB | EB | EB | EB | EB |
| Catalyst System Solvent Mass (g) | 1 | 1 | 1 | 1 | 1 | 1 |
| MAO Type | MMAO-20 | MMAO-20 | MMAO-20 | MMAO-20 | MMAO-20 | MMAO-3 |
| Mass MAO (g) | 1.50 | 1.50 | 1.36 | 1.36 | 1.36 | 1.275 |
| Al:Cr ratio | 500 | 554 | 610 | 610 | 610 | 554 |
| Catalyst System Aging Time (hours) | 0.5 | 0.5 | 0.5 | 0.5 | 1.5 | 0.5 |
| Ethylene Oligomerization Conditions | | | | | | |
| Organic Reaction Medium** | Cy | Cy | Cy | Cy | Cy | Cy |
| Organic Reaction Medium Volume (mL) | 200 | 200 | 200 | 200 | 200 | 200 |
| Ethylene Pressure (psi) | 875 | 875 | 875 | 875 | 875 | 875 |
| Hydrogen Pressure (psi) | 50 | 50 | 50 | 50 | 50 | 50 |
| Oligomerization Temperature (° C.) | 70 | 70 | 70 | 70 | 70 | 70 |
| Oligomerization Time (minutes) | 35 | 20 | 20 | 35 | 20 | 20 |
| Oligomer Product | | | | | | |
| Liquid Oligomer Product (grams) | 5 | 4 | 3 | 5 | 75 | 148 |
| Polymer (grams) | 0 | 0.72 | 0.06 | 0.17 | 0.66 | 0.09 |
| Polymer (wt. %) | 0.00% | 15.17% | 2.56% | 3.3 | 0.88% | 0.06 |
| Liquid Oligomer Product Distribution | | | | | | |
| Combined $C_6 + C_8$ (wt. %) | 97.0 | 98.6 | 97.3 | 96.1 | 92.6 | 95.7 |
| $C_6$ (wt. %) | 66.0 | 94.8 | 56.3 | 41.2 | 35.3 | 94.8 |
| 1-hexene (wt. % of $C_6$ product) | 93.8 | 96.2 | 91.2 | 88.2 | 78.3 | 99.59 |
| Methylcyclopentane (wt. % of $C_6$ product) | 3.0 | 1.3 | 3.9 | 5.6 | 10.0 | 0.03 |
| Methylenecyclopentane (wt. % of $C_6$ product) | 2.0 | 1.4 | 2.7 | 4.2 | 8.1 | 0.02 |
| $C_8$ (wt. %) | 31.0 | 3.8 | 41.0 | 54.9 | 57.3 | 0.9 |
| 1-octene (wt. % of $C_8$ product) | 96.6 | 91.5 | 95.3 | 95.3 | 93.4 | 99.1 |
| $C_{10+}$ (wt. %) | 3.0 | 1.4 | 2.7 | 3.9 | 7.8 | 4.3 |
| $C_{10}$ (wt. %) | 2.1 | 1.4 | 2.7 | 2.9 | 4.1 | 4.2 |
| $C_{12}$ (wt. %) | 0.9 | 0 | 0 | 1.0 | 3.3 | 0.1 |
| $C_{14+}$ (wt. %) | 0 | 0 | 0 | 0 | 0 | 0.0 |
| Ethylene Oligomerization Productivities and Activities | | | | | | |
| Grams ($C_6 + C_8$)/gram Cr | 12,886 | 10,832 | 11,066 | 15,490 | 228,993 | 454,667 |
| Grams ($C_6 + C_8$)/gram Cr/hour | 38,659 | 32,496 | 33,199 | 26,554 | 686,980 | 1,364,001 |

*EB = ethylbenzene
**Cy = cyclohexane

The subject matter of the present disclosure illustratively disclosed herein suitably can be practiced in the absence of any element that is not specifically disclosed herein and/or any optional element disclosed herein. While compositions and processes are described in terms of "comprising," "containing," or "including" various components or steps, the compositions and processes can also "consist essentially of" or "consist of" the various components and steps. All numbers and ranges disclosed above can vary by some amount. Whenever a numerical range with a lower limit and an upper limit is disclosed, any number and any included range falling within the range are specifically disclosed. In particular, every range of values of the form, "from about a to about b," or, equivalently, "from approximately a to b," or, equivalently, "from approximately a-b" disclosed herein is to be understood to set forth every number and range encompassed within the broader range of values.

All publications, patents, and published patent applications mentioned herein are incorporated herein by reference in their entirety. The publications and patents mentioned herein can be utilized for the purpose of describing and disclosing, for example, the constructs and methodologies that are described in the publications, which might be used in connection with the presently described subject matter. The publications discussed throughout the text are provided solely for their disclosure prior to the filing date of the present application. Nothing herein is to be construed as an admission that the applicants are not entitled to antedate such disclosure by virtue of prior investigations, including but not limited to experimental results.

Therefore, the subject matter of the present disclosure is well adapted to attain the ends and advantages mentioned as well as those that are inherent therein. This concludes the detailed description. The particular embodiments disclosed above are illustrative only, as the subject matter of the present disclosure can be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above can be altered or modified and all such variations are considered within the scope and spirit of the present disclosure. Accordingly, the protection sought herein is as set forth in the claims below.

What is claimed is:

1. A catalyst system comprising
i) a heterocyclic 2-[(phosphinyl)aminyl]imine transition metal compound complex having Structure HCPAITMC 1

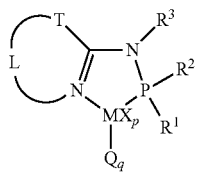

Structure HCPAITMC 1 wherein

T is oxygen or sulfur, $R^1$ and $R^2$ are each independently a $C_1$ to $C_{20}$ organyl group consisting essentially of inert functional groups, $R^3$ is hydrogen or a $C_1$ to $C_{20}$ organyl group, L is a $C_1$ to $C_{20}$ organylene group consisting essentially of inert functional groups, $MX_p$ represents a transition metal compound where M is chromium, X is a monoanion, and p is an integer from 1 to 6, Q is a neutral ligand, and q ranges from 0 to 6, and ii) are organoaluminum compound.

2. The catalyst system of claim 1, wherein the heterocyclic 2-[(phosphinyl)aminyl]imine transition metal compound complex has Structure HCPAITMC 2, Structure HCPAITMC 3, Structure HCPAITMC 4, Structure HCPAITMC 5, or Structure HCPAITMC 6

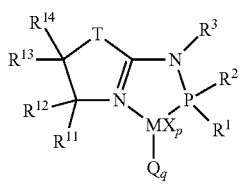

Structure HCPAITMC 2

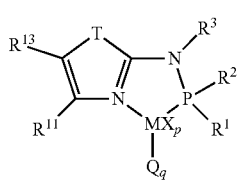

Structure HCPAITMC 3

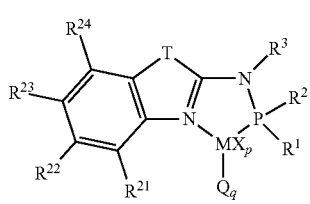

Structure HCPAITMC 4

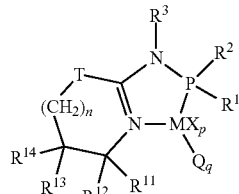

Structure HCPAITMC 5

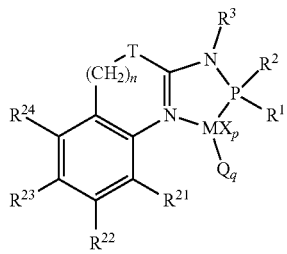

Structure HCPAITMC 6 wherein n is 1 or 2,

T is oxygen or sulfur, $R^1$ and $R^2$ are each independently a $C_1$ to $C_{20}$ organyl group consisting essentially of inert functional groups, $R^3$ is hydrogen or a $C_1$ to $C_{20}$ organyl group, $R^{11}$, $R^{12}$, $R^{13}$, $R^{14}$, $R^{21}$, $R^{22}$, $R^{23}$, and $R^{24}$ are each independently hydrogen or a $C_1$ to $C_{20}$ organyl group consisting essentially of inert functional groups, optionally $R^{11}$ or $R^{12}$ and $R^{13}$ or $R^{14}$ are joined to form a ring or ring system, $MX_p$ represents a transition metal compound where M is chromium, X is a monoanion, and p is an integer from 2 to 6, Q is a neutral ligand, and q ranges from 0 to 6.

3. The catalyst system of claim 2, wherein
$R^{11}$ and $R^{21}$ are each independently hydrogen or a $C_1$ to $C_{10}$ alkyl group, and
$R^{12}$, $R^{13}$, $R^{14}$, $R^{22}$, $R^{23}$, and $R^{24}$ are hydrogen.

4. The catalyst system of claim 2, wherein $R^3$ is hydrogen.

5. The catalyst system of claim 1, wherein the transition metal compound comprises a chromium(III) carboxylate, a chromium(III) β-diketonate, or a chromium(III) halide.

6. The catalyst system of claim 1, wherein the organoaluminum compound comprises an aluminoxane.

7. The catalyst system of claim 6, wherein the aluminoxane comprises methylaluminoxane, a modified methylaluminoxane, ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, or mixtures thereof.

8. The catalyst system of claim 6, wherein the aluminoxane comprises a modified methylaluminoxane.

9. The catalyst system of claim 6, wherein an aluminum of the aluminoxane to transition metal of the heterocyclic 2-[(phosphinyl)aminyl]imine transition metal compound complex molar ratio is in the range of from 10:1 to 5,000:1.

10. The catalyst system of claim 1, wherein the heterocyclic 2-[(phosphinyl)aminyl]imine transition metal compound complex has Structure HCPAITMC 2, Structure HCPAITMC 3, Structure HCPAITMC 4, Structure HCPAITMC 5, or Structure HCPAITMC 6

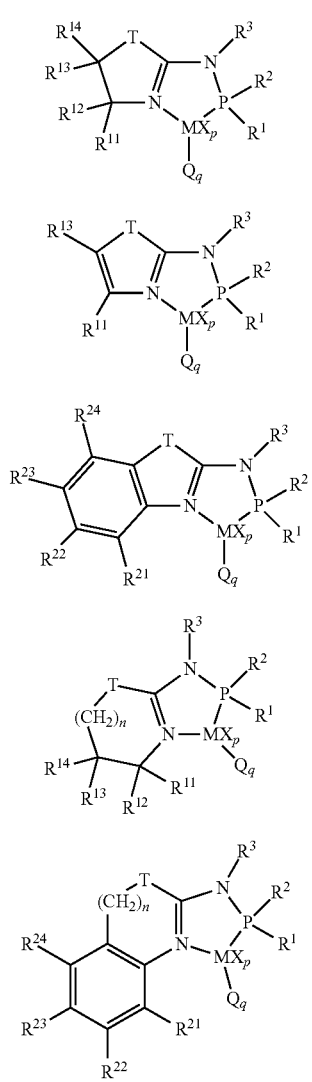

Structure HCPAITMC 2

Structure HCPAITMC 3

Structure HCPAITMC 4

Structure HCPAITMC 5

Structure HCPAITMC 6

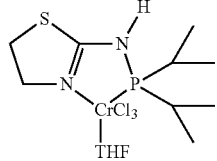

Structure HCPAlCr A

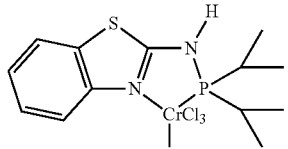

Structure HCPAlCr B

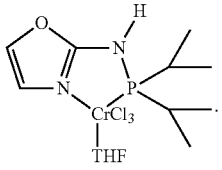

Structure HCPAlCr C

12. A process comprising:

contacting i) ethylene, ii) a catalyst system comprising (a) a heterocyclic 2-[(phosphinyl)aminyl]imine transition metal compound complex having Structure HCPAITMC 1

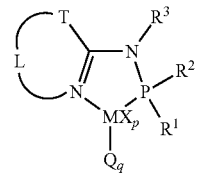

Structure HPAITMC 1 wherein n is 1 or 2,

T is oxygen or sulfur, $R^1$ and $R^2$ are each independently a $C_1$ to $C_{20}$ organyl group consisting essentially of inert functional groups, $R^3$ is hydrogen, $R^{11}$ and $R^{21}$ are each independently hydrogen or a $C_1$ to $C_{10}$ alkyl group, $R^{12}$, $R^{13}$, $R^{14}$, $R^{22}$, $R^{23}$, and $R^{24}$ are hydrogen, $MX_p$, is chromium(III) chloride, Q is a neutral ligand, q ranges from 0 to 3, the organoaluminum compound is an aluminoxane, and an aluminum of the aluminoxane to chromium of the heterocyclic 2-[(phosphinyl)aminyl])imine transition metal compound complex molar ratio is in the range of from 10:1 to 5,000:1.

11. The catalyst system of claim 10, wherein the heterocyclic 2-[(phosphinyl)aminyl]imine transition metal compound complex has Structure HCPAlCr A, Structure HCPAlCr B, or Structure HCPAlCrC.

wherein

T is oxygen or sulfur, $R^1$ and $R^2$ are each independently a $C_1$ to $C_{20}$ organyl group consisting essentially of inert functional groups, $R^3$ is hydrogen or a $C_i$ to $C_{20}$ organyl group, L is a $C_1$ to $C_{20}$ organylene group consisting essentially of inert functional groups, $MX_p$ represents a transition metal compound where M is chromium, X is a monoanion, and p is an integer from 1 to 6, Q is a neutral ligand, q ranges from 0 to 6, and (b) an organoaluminum compound, and iii) optionally hydrogen to form an oligomer product.

13. The process of claim 12, wherein the heterocyclic 2-[(phosphinyl)aminyl]imine transition metal compound complex has Structure HCPAITMC 2, Structure HCPAITMC 3, Structure HCPAITMC 4, Structure HCPAITMC 5, or Structure HCPAITMC 6

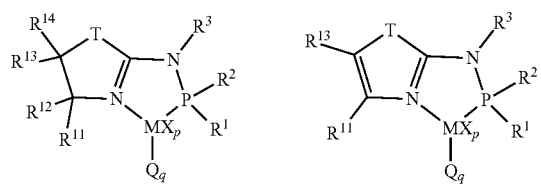

Structure HCPAITMC 2    Structure HCPAITMC 3

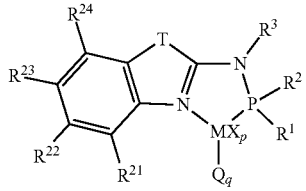

Structure HCPAITMC 4

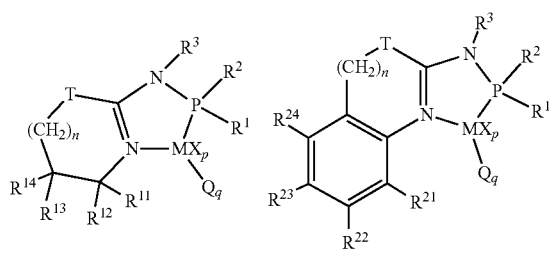

Structure HCPAITMC 5    Structure HCPAITMC 6

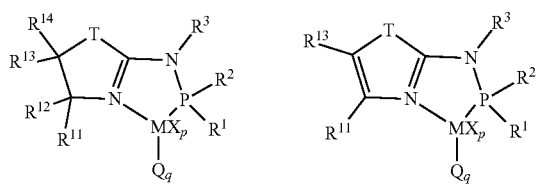

Structure HCPAITMC 2    Structure HCPAITMC 3

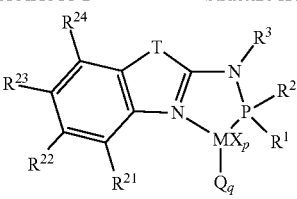

Structure HCPAITMC 4

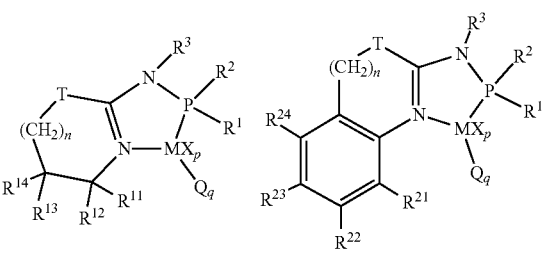

Structure HCPAITMC 5    Structure HCPAITMC 6 wherein n is 1 or 2,

T is oxygen or sulfur, $R^1$ and $R^2$ are each independently a $C_1$ to $C_{20}$ organyl group consisting essentially of inert functional groups, $R^3$ is hydrogen or a $C_1$ to $C_{20}$ organyl group, $R^{11}$, $R^{12}$, $R^{13}$, $R^{14}$, $R^{21}$, $R^{22}$, $R^{23}$, and $R^{24}$ are each independently hydrogen or a $C_1$ to $C_{20}$ organyl group consisting essentially of inert functional groups, optionally $R^H$ or $R^{12}$ and $R^{13}$ or $R^{14}$ are joined to form a ring or ring system, $MX_p$ represents a transition metal compound where M is chromium, X is a monoanion, and p is an integer from 1 to 6, Q is a neutral ligand, and q ranges from 0 to 6.

14. The process of claim 12, wherein the process further comprises contacting the heterocyclic 2-[(phosphinyl)aminyl]imine transition metal compound complex and the organoaluminum compound to form a catalyst system mixture, and aging the catalyst system mixture in a substantial absence of ethylene to form an aged catalyst system mixture.

15. The process of claim 14, wherein the catalyst system is aged in the substantial absence of ethylene for from 5 minutes to 6 hours.

16. The process of claim 12, wherein the transition metal compound comprises a chromium(III) carboxylate, a chromium(III) β-diketonate, or a chromium(III) halide.

17. The process of claim 12, wherein the organoaluminum compound comprises an aluminoxane.

18. The process of claim 12, wherein the heterocyclic 2-[(phosphinyl)aminyl]imine transition metal compound complex has Structure HCPAITMC 2, Structure HCPAITMC 3, Structure HCPAITMC 4, Structure HCPAITMC 5, or Structure HCPAITMC 6 wherein n is 1 or 2,

T is oxygen or sulfur, $R^1$ and $R^2$ are each independently a $C_1$ to $C_{20}$ organyl group consisting essentially of inert functional groups, $R^3$ is hydrogen, $R^{11}$ and $R^{21}$ are each independently hydrogen or a $C_1$ to $C_{10}$ alkyl group, $R^{12}$, $R^{13}$, $R^{14}$, $R^{22}$, $R^{23}$, and $R^{24}$ are hydrogen, $MX_p$ is chromium(III) chloride, Q is a neutral ligand, q ranges from 0 to 6, and the organoaluminum compound is an aluminoxane.

19. The process of claim 18, wherein the oligomer product is formed at (a) an ethylene partial pressure ranging from 150 psi to 2,000 psi, (b) a hydrogen partial pressure ranging from 5 psi to 400 psi, (c) a temperature ranging from 20 ° C. to 150 ° C., and (d) an aluminum of the aluminoxane to chromium of the heterocyclic 2-[(phosphinyl)aminyl]imine transition metal compound complex molar ratio is in the range of from 10:1 to 5,000:1.

20. The process of claim 19, wherein the heterocyclic 2-[(phosphinyl)aminyl]imine transition metal compound complex has Structure HCPAlCr A, Structure HCPAlCr B, or Structure HCPAlCr C

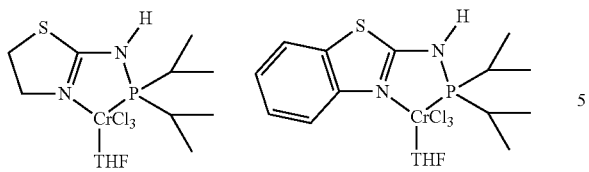
Structure HCPAlCr A        Structure HCPAlCr B
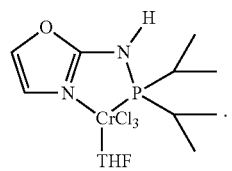
Structure HCPAlCr C
21. The process of claim 12, wherein the oligomer product comprises at least 70 wt. % ethylene trimer, ethylene tetramer, or any combination thereof
22. The process of claim 21, wherein the ethylene trimer comprises at least 85 wt. % 1-hexene
23. The process of claim 21, wherein the ethylene tetramer comprises at least 90 wt. % 1-octene.
* * * * *